(12) United States Patent
LaChappelle et al.

(10) Patent No.: US 10,561,564 B2
(45) Date of Patent: Feb. 18, 2020

(54) LOW PROFILE EXOSKELETON

(71) Applicant: Unlimited Tomorrow, Inc., Durango, CO (US)

(72) Inventors: Easton J. LaChappelle, Durango, CO (US); Aaron Blue, Durango, CO (US)

(73) Assignee: Unlimited Tomorrow, Inc., Rhinebeck, NY (US)

( * ) Notice: Subject to any disclaimer, the term of this patent is extended or adjusted under 35 U.S.C. 154(b) by 1140 days.

(21) Appl. No.: 14/933,584

(22) Filed: Nov. 5, 2015

(65) Prior Publication Data

US 2016/0128890 A1    May 12, 2016

Related U.S. Application Data

(60) Provisional application No. 62/076,716, filed on Nov. 7, 2014.

(51) Int. Cl.
| | |
|---|---|
| *A61H 3/00* | (2006.01) |
| *B25J 9/00* | (2006.01) |
| *A61H 1/02* | (2006.01) |
| *A61F 2/60* | (2006.01) |
| *A61F 2/68* | (2006.01) |
| *A61F 5/01* | (2006.01) |

(52) U.S. Cl.
CPC ............... *A61H 3/00* (2013.01); *A61F 2/60* (2013.01); *B25J 9/0006* (2013.01); *A61F 2/68* (2013.01); *A61F 2005/0155* (2013.01); *A61H 1/0237* (2013.01); *A61H 1/0262* (2013.01)

(58) Field of Classification Search
CPC ... B25J 9/0006; A61F 2/60; A61F 2/68; A61F 2005/0155; A61F 2002/6845; A61H 3/00; A61H 1/0237; A61H 1/0262; A61H 2201/1215; A61H 2201/164; A61H 2201/165

See application file for complete search history.

(56) References Cited

U.S. PATENT DOCUMENTS

| | | |
|---|---|---|
| D650,566 S | 12/2011 | Yamashita et al. |
| 8,749,527 B2 | 6/2014 | Douxchamps et al. |
| D709,038 S | 7/2014 | Takama et al. |
| 8,773,148 B2 | 7/2014 | Sankai et al. |
| 8,801,641 B2 | 8/2014 | Kazerooni et al. |
| 8,894,592 B2 | 11/2014 | Amundson et al. |
| 8,905,955 B2 | 12/2014 | Goffer et al. |
| 8,945,028 B2 | 2/2015 | Kazerooni et al. |
| 8,968,222 B2 | 3/2015 | Kazerooni et al. |

(Continued)

*Primary Examiner* — David H Willse
*Assistant Examiner* — Javier G Blanco
(74) *Attorney, Agent, or Firm* — Lerner, David, Littenberg, Krumholz & Mentlik, LLP

(57) ABSTRACT

A mobility enhancing device in the form of an exoskeleton provides mobility assistance or enhancement to a user within the exoskeleton. The exoskeleton may include a torso support and two leg supports coupled to the torso support. Each leg support may include a hip joint, a knee joint, a foot module, and panels connecting the torso support to the hip joints, the hip joints to the knee joints, and the knee joints to the foot modules. Actuators such as motors may be positioned in a discrete location on exoskeleton away from the relatively bulky knee and hip joints to provide for a low profile of the exoskeleton, which may allow the exoskeleton to be worn inconspicuously under a user's clothing.

14 Claims, 34 Drawing Sheets

(56) References Cited

U.S. PATENT DOCUMENTS

| | | | |
|---|---|---|---|
| 9,011,354 B2 | 4/2015 | Angold et al. | |
| 2008/0156363 A1* | 7/2008 | Ikeuchi | A61H 3/00 135/65 |
| 2010/0121232 A1* | 5/2010 | Sankai | A61H 3/008 601/23 |
| 2010/0271051 A1 | 10/2010 | Sankai et al. | |
| 2011/0214524 A1* | 9/2011 | Jacobsen | A61F 2/68 74/490.04 |
| 2012/0271207 A1* | 10/2012 | Schoen | A61F 5/0102 601/34 |
| 2013/0231595 A1 | 9/2013 | Zoss et al. | |
| 2013/0237884 A1 | 9/2013 | Kazerooni et al. | |
| 2013/0303950 A1 | 11/2013 | Angold et al. | |
| 2014/0100492 A1* | 4/2014 | Nagasaka | A61H 3/061 601/34 |
| 2014/0364755 A1 | 12/2014 | Sankai et al. | |
| 2015/0045703 A1 | 2/2015 | Strausser et al. | |
| 2015/0134078 A1 | 5/2015 | Amundson et al. | |
| 2015/0173993 A1* | 6/2015 | Walsh | B25J 9/0006 414/4 |
| 2015/0190249 A1* | 7/2015 | Ishibashi | A61H 3/00 623/24 |
| 2015/0226234 A1 | 8/2015 | Amundson et al. | |

\* cited by examiner

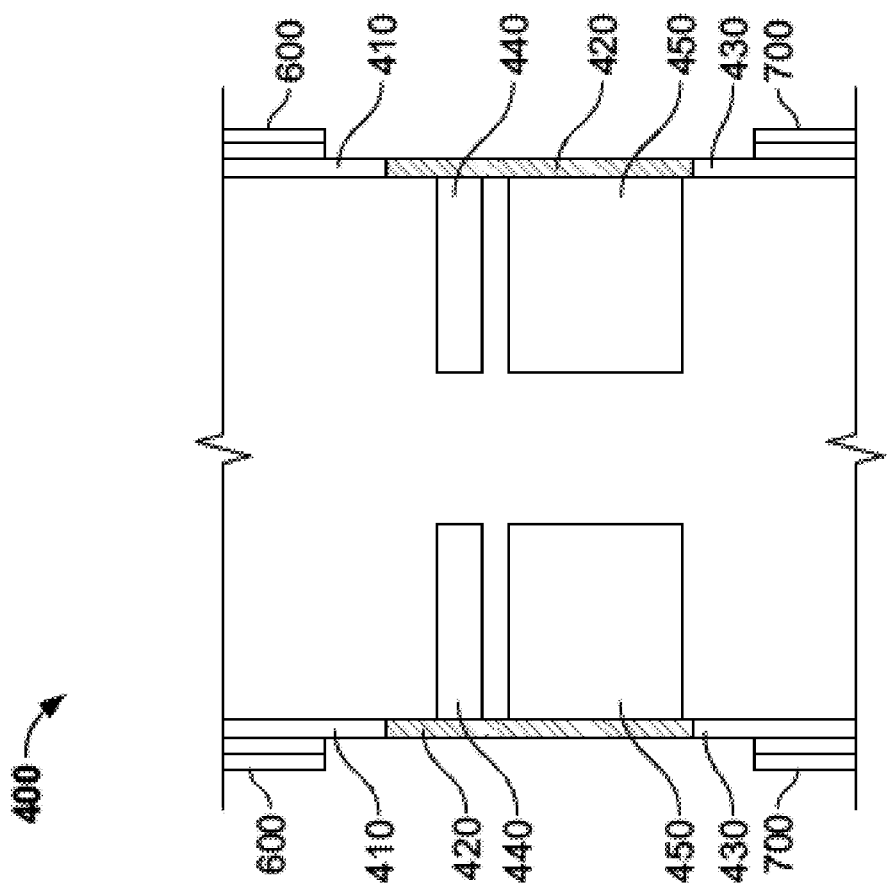
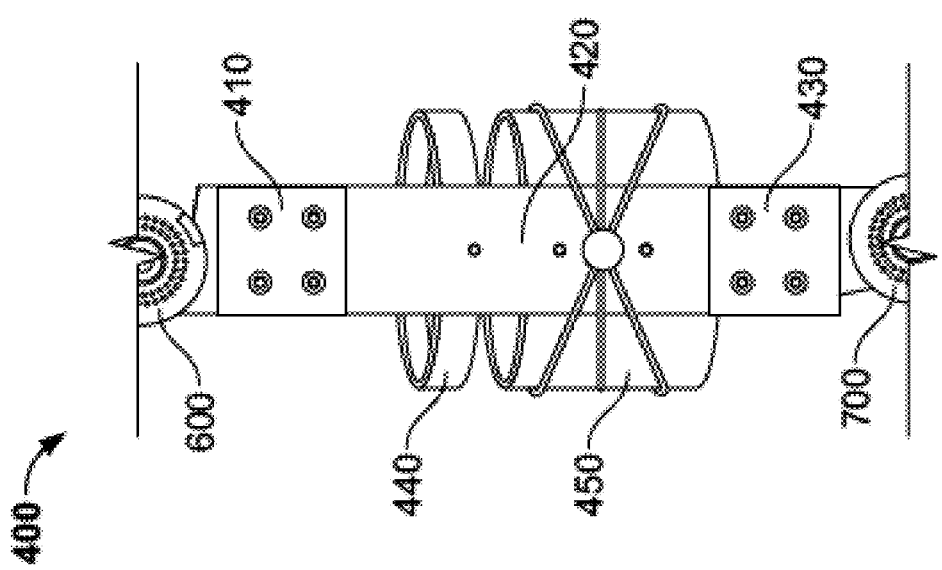
FIG. 3B
FIG. 3A

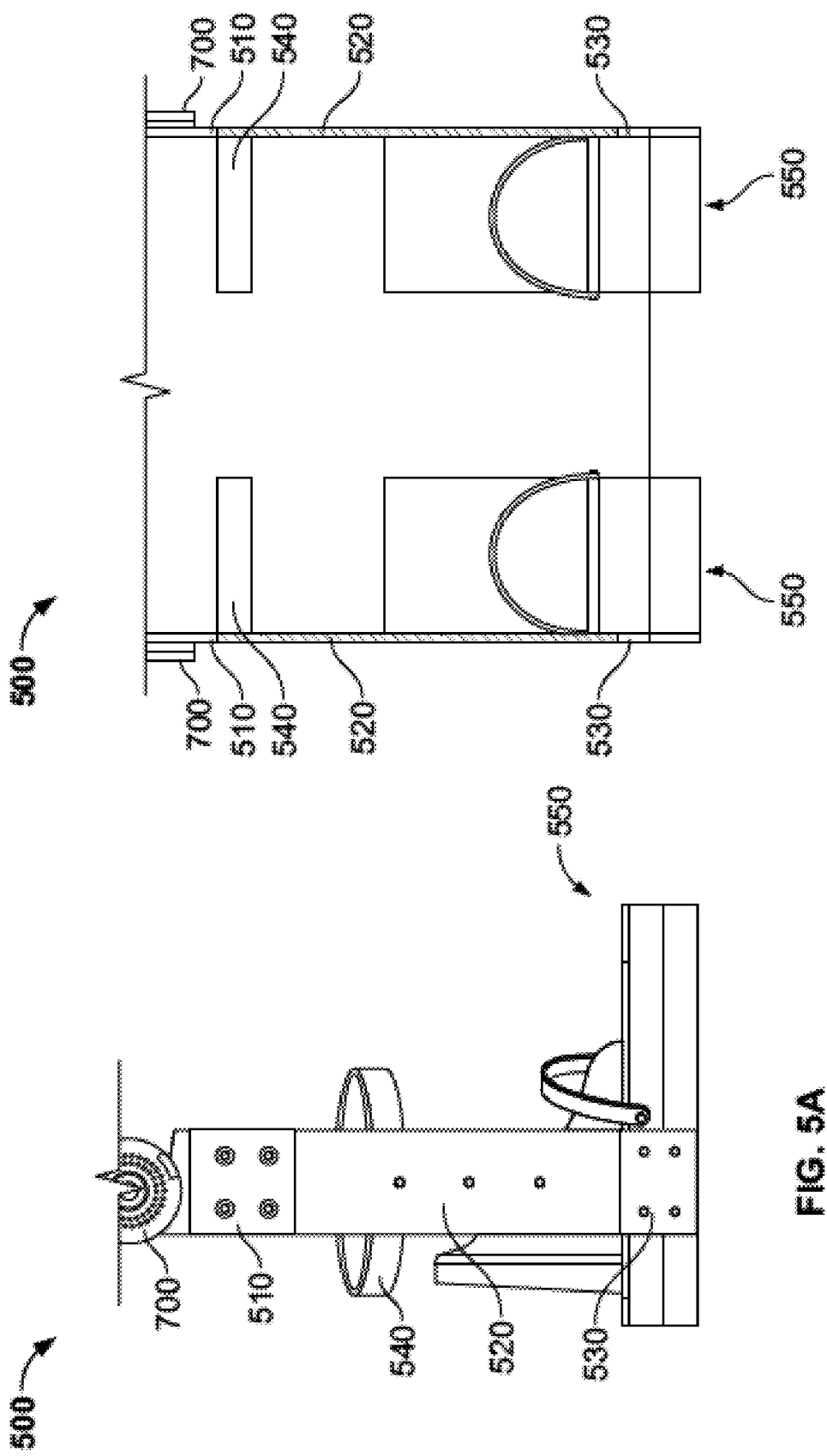

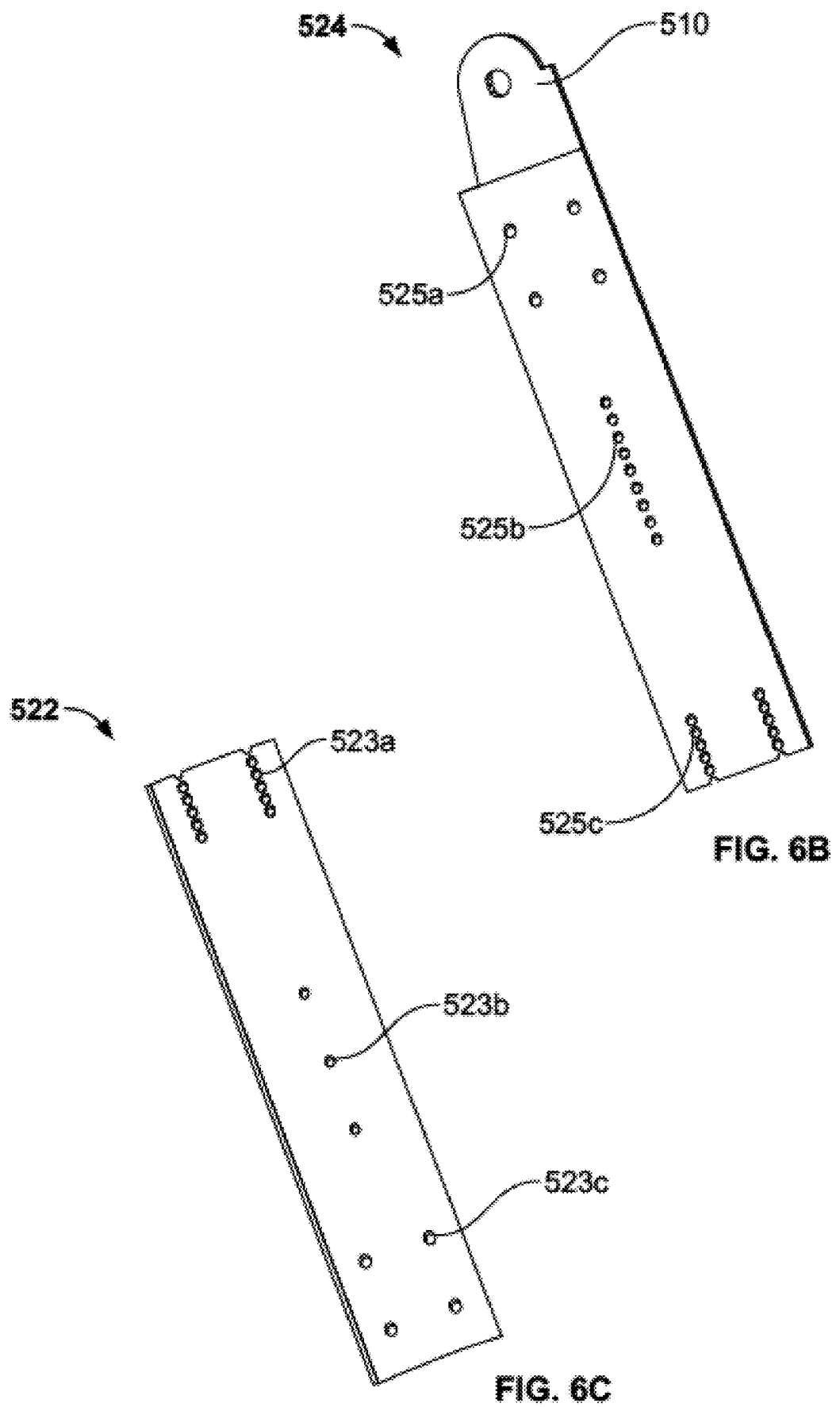

LOW PROFILE EXOSKELETON

CROSS-REFERENCE TO RELATED APPLICATIONS

This application claims the benefit of the filing date of U.S. Provisional Patent Application No. 62/076,716, filed Nov. 7, 2014, the disclosure of which is hereby incorporated by reference herein.

BACKGROUND

Interest in mobility enhancing devices, such as artificial exoskeletons, has been increasing. Exoskeleton devices may take different forms, generally being powered devices with structures to support and/or enhance a user's mobility. For example, exoskeleton devices may be coupled to a user having some degree of lower body weakness to restore some level of mobility to the user. Mobility may be restored, for example, by reducing or eliminating the need for other assistive devices, such as walkers, crutches, wheelchairs, etc.

Exoskeleton devices may have one or more joints, the movement of which is caused by an actuator or other power transfer device such as a motor, which in turn may be controlled by a control system, and powered by a power supply. As such, exoskeleton devices may include a number of components in addition to the basic structural units of the exoskeleton. Often, these additional components are contained within a backpack worn by the user. Similarly, the basic structural units of the exoskeleton are often strapped over a user's clothing. Such a configuration may result in the use of an exoskeleton device being highly conspicuous. Particularly for a user with some level of disability, a highly conspicuous exoskeleton may draw undesired attention.

BRIEF SUMMARY

According to one aspect of the invention, a mobility assisting device comprises an exoskeleton having at least one leg support having at least one hip joint and at least one knee joint. The leg support is configured to be coupled to a user so that the hip joint substantially aligns with a hip joint of the user and the knee joint substantially aligns with the knee joint of the user. The hip joint is driven by a hip joint motor and the knee joint is driven by a knee joint motor. The knee joint motor is positioned remotely from the knee joint and the hip joint motor is positioned remotely from the hip joint. This positioning may help reduce the profile of the exoskeleton, particularly near the joints.

According to another aspect of the disclosure, a mobility assisting device may comprise a torso support, a hip joint, a knee joint, a foot support, a first structure coupling the torso support to the hip joint, a second structure coupling the hip joint to the knee joint, a third structure coupling the knee joint to the foot support, and a compartment having a hip joint actuation device and a knee joint actuation device, wherein the hip joint actuation device is operably coupled to the hip joint, the hip joint actuation device configured to drive both flexion and extension of the hip joint, and wherein the knee joint actuation device is operably coupled to the knee joint, the knee joint actuation device configured to drive both flexion and extension of the hip joint; and/or the compartment is positioned within the foot support; and/or the compartment is positioned on the first structure coupling the torso support to the hip joint; and/or the compartment is positioned on the second structure coupling the hip joint to the knee joint; and/or the compartment is positioned on or within the torso support; and/or the compartment is positioned on the third structure coupling the knee joint to the foot support; and/or a single hip cable couples the hip joint actuation device to the hip joint, the single hip cable configured to transmit power from the hip joint actuation device for driving both flexion and extension of the hip joint; and/or at least a portion of the single hip cable is housed within a hollow conduit, the single hip cable configured to move through the tube-like conduit; and/or a single knee cable couples the knee joint actuation device to the knee joint, the single knee cable configured to transmit power from the knee joint actuation device for driving both flexion and extension of the knee joint; and/or at least a portion of the single knee cable is housed within a hollow conduit, the single knee cable configured to move through the tube-like conduit; and/or at least two knee cables couple the knee joint actuation device to the knee joint, a first knee cable configured to transmit power from the knee joint actuation device for driving flexion of the knee joint and a second knee cable configured to transmit power form the knee joint actuation device for driving extension of the knee joint; and/or the hip joint includes a hip extension spindle coupled to a hip flexion spindle, the hip extension spindle configured to rotate in a first direction to cause extension of the first structure relative to the second structure, the hip flexion spindle configured to rotate in a second direction opposite the first direction to cause flexion of the first structure relative to the second structure; and/or a cable that couples the hip joint actuation device to the hip joint, wherein a first end of the cable is coupled to the hip flexion spindle and a second end of the cable is coupled to hip the extension spindle, a middle portion of the cable being operably coupled to the hip joint actuation device, the cable configured to transmit power from the hip joint actuation device for driving either flexion or extension of the hip joint; and/or the knee joint includes a knee extension spindle coupled to a knee flexion spindle, the knee extension spindle configured to rotate in a first direction to cause extension of the second structure relative to the third structure, the knee flexion spindle configured to rotate in a second direction opposite the first direction to cause flexion of the second structure relative to the third structure; and/or a cable that couples the knee joint actuation device to the knee joint, wherein a first end of the cable is coupled to the flexion spindle and a second end of the cable is coupled to the extension spindle, a middle portion of the cable being operably coupled to the hip joint actuation device, the cable configured to transmit power from the hip joint actuation device for driving both flexion and extension of the hip joint; and/or the foot support includes an upper platform coupled to a lower platform, the compartment being defined by an interior volume between the upper platform and lower platform; and/or the second structure coupling the hip joint to the knee joint includes a first panel configured to be adjustably coupled to a second panel, the first panel being coupled to the hip joint and the second panel being coupled to the knee joint; and/or the third structure coupling the knee joint to the foot support includes a first panel configured to be adjustably coupled to a second panel, the first panel being coupled to the knee joint and the second panel being coupled to the foot support; and/or the first support includes an inferior first support bracket and the second support includes a superior second support bracket, the inferior first support bracket and superior second support bracket having a first set of corresponding surfaces for limiting a maximum extension of the hip joint and a second set of corresponding surfaces for limiting a maximum flexion of the hip joint; and/or the second support includes an inferior second support bracket and the third support includes a superior third support bracket, the inferior second support bracket and superior third support bracket having a first set of corresponding surfaces for limiting a maximum extension of the knee joint and a second set of corresponding surfaces for limiting a maximum flexion of the knee joint; and/or the foot support includes at least one sensor selected from the group consisting of weight sensors, inertial measurement unit sensors, and accelerometers.

BRIEF DESCRIPTION OF THE DRAWINGS

FIG. 3A is an isolated side view of an upper leg section of the exoskeleton.

FIG. 3B is an isolated front view of the upper leg section of FIG. 3A.

FIG. 5A is an isolated side view of a lower leg section of the exoskeleton.

FIG. 5B is an isolated front view of the lower leg section of FIG. 5A.

FIGS. 6B-C are perspective views of the outer surfaces of components of the lower leg panel of FIG. 6A.

DETAILED DESCRIPTION

Figure 1A:
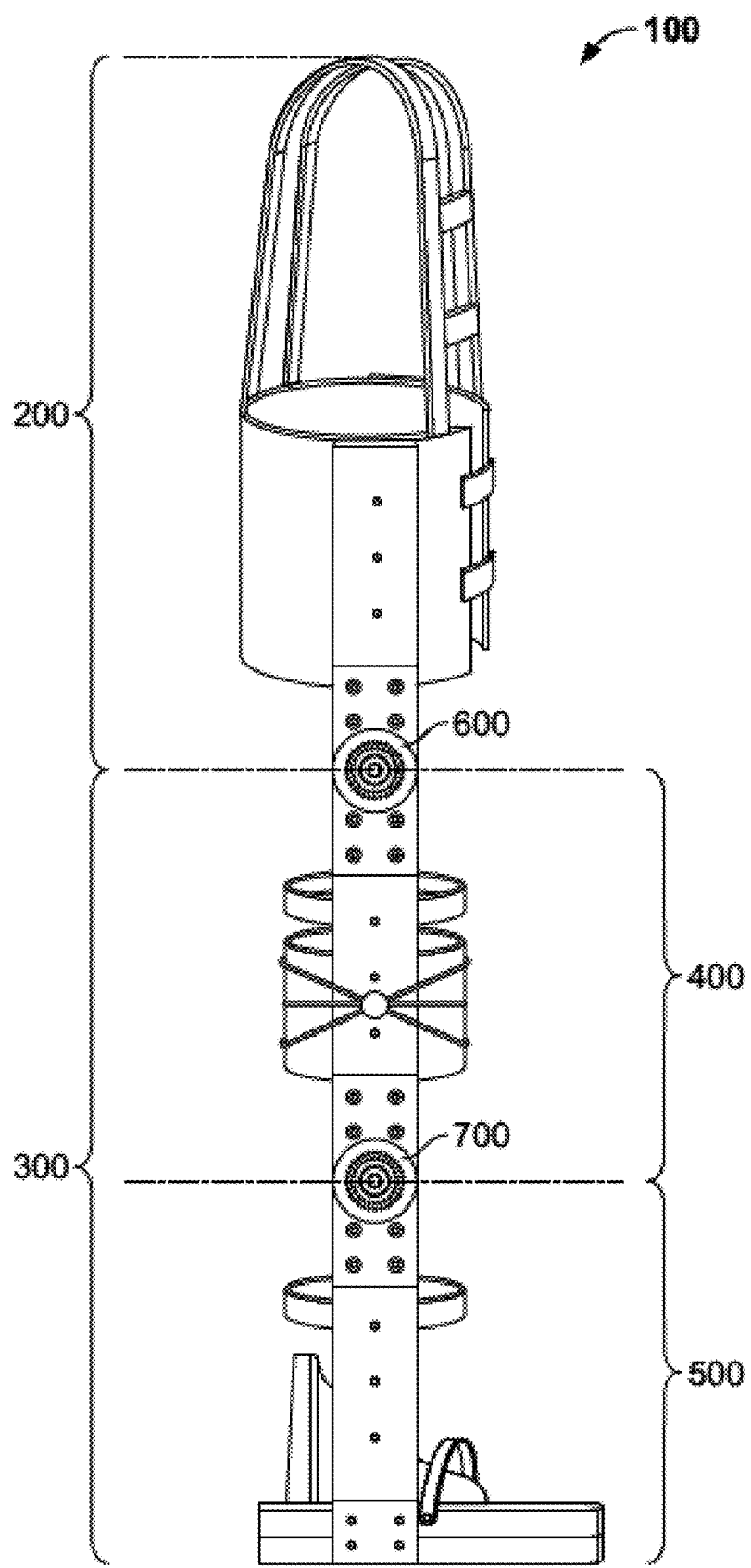
FIG. 1A is a side view of a low profile exoskeleton according to one embodiment of the disclosure.
Figure 1B:
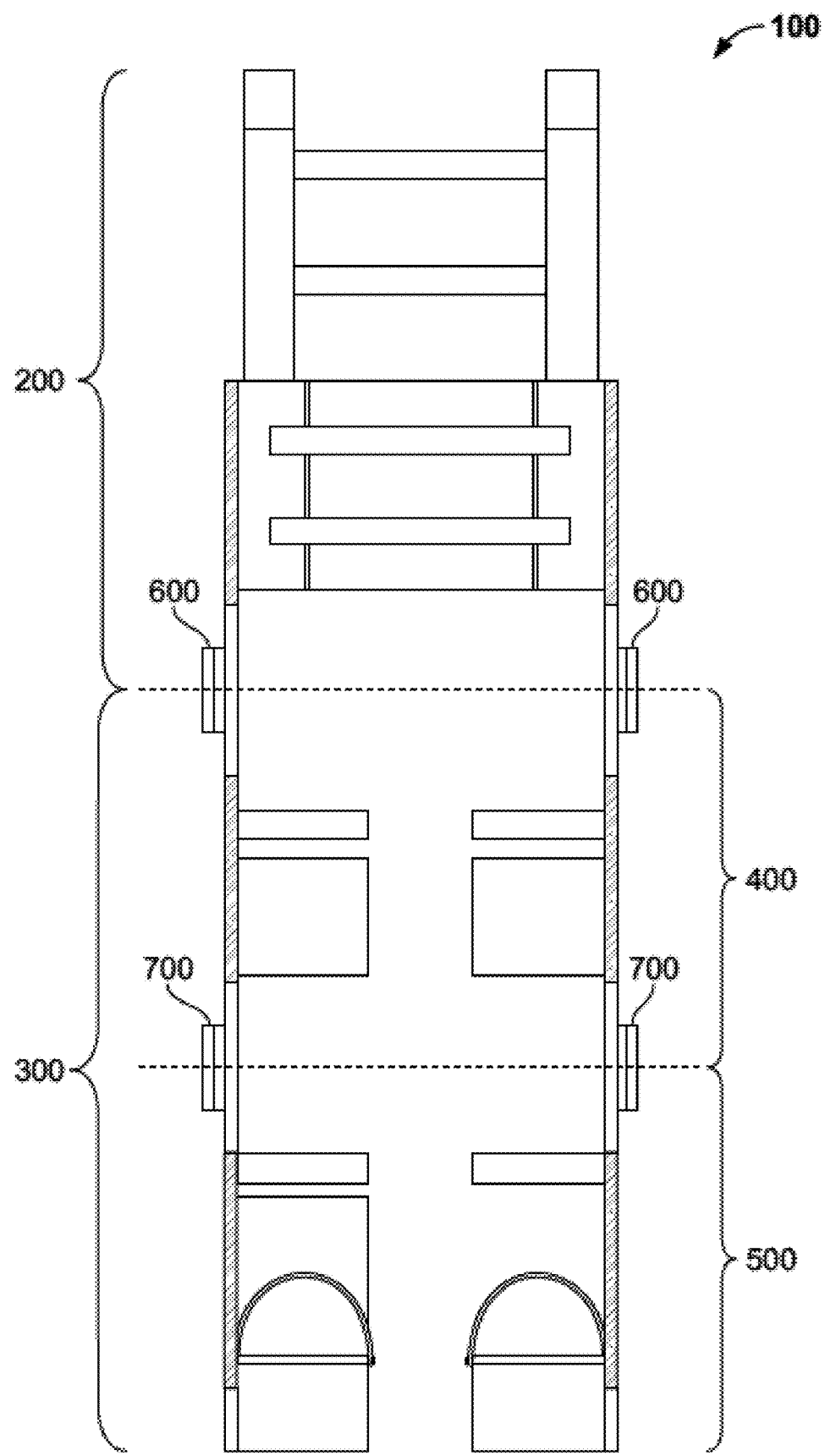
FIG. 1B is a front view of the exoskeleton of FIG. 1A.
Figure 1C:
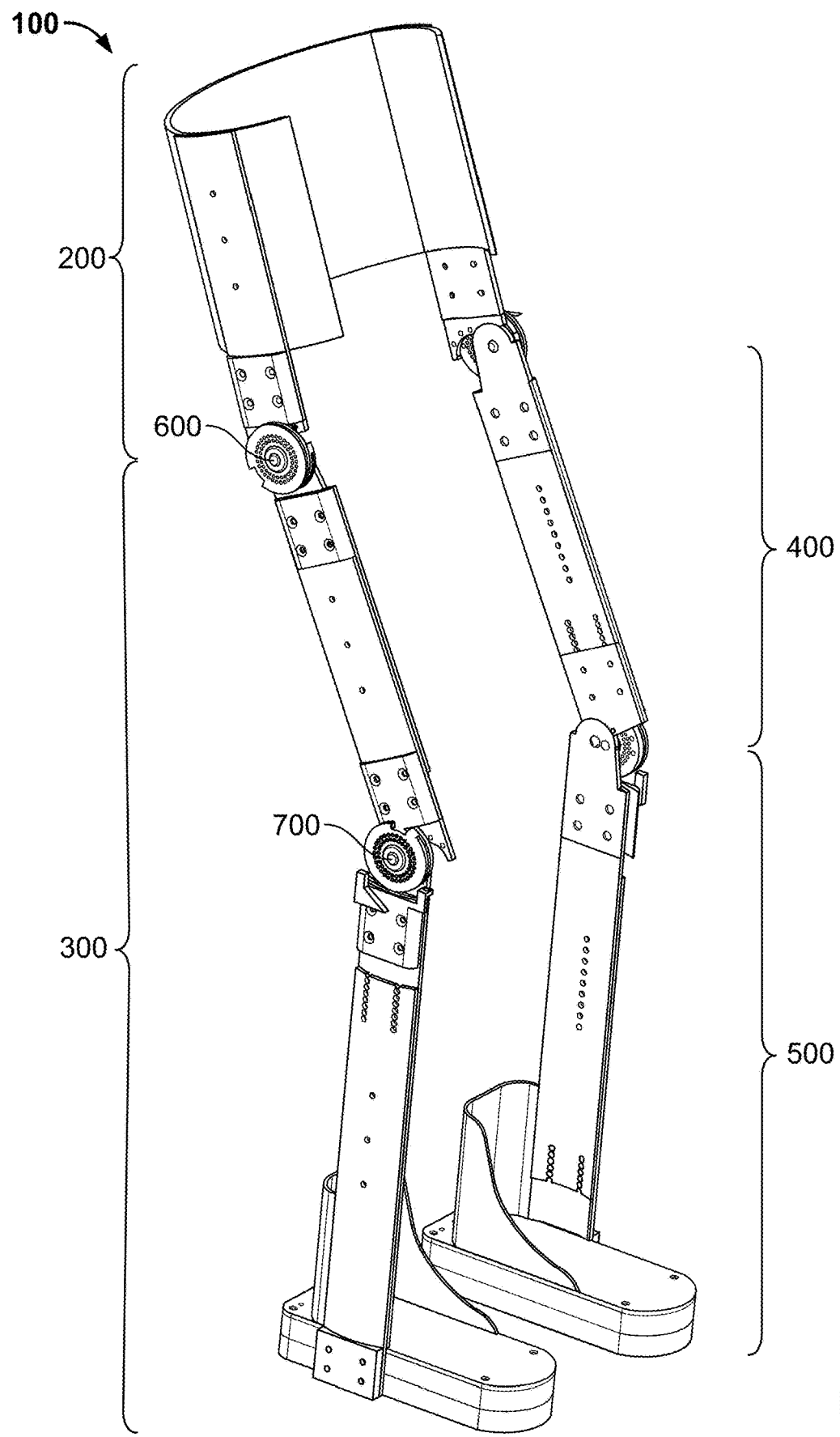
FIG. 1C is a perspective view of the exoskeleton of FIG. 1A with certain components omitted.

FIGS. 1A-C illustrate a low profile exoskeleton 100 according to one embodiment of the disclosure. Generally, exoskeleton 100 may include an upper extremity portion 200 configured to support the torso of a user and a lower extremity portion 300 configured to support the lower extremities of a user. Lower extremity portion 300 may include an upper leg section 400 and a lower leg section 500. Exoskeleton 100 may also include a pair of hip actuators 600 and a pair of knee actuators 700, with a center of the hip actuators 600 defining the boundary between the upper extremity portion 200 and the lower extremity portion 300, and a center of the knee actuators 700 defining the boundary between the upper leg section 400 and the lower leg section 500. Hip actuators 600 provide for relative angular motion between upper extremity section 200 and upper leg section 400, while knee actuators 700 provide for relative angular motion between upper leg section 400 and lower leg section 500. Thus, with the user's torso and lower extremities supported by the upper extremity portion 200 and the lower extremity portion 300, respectively, hip actuators 600 and knee actuators 700 assist a user in performing a number of tasks, such as standing, walking, climbing, etc. Preferably, when exoskeleton 100 is in use, hip actuators 600 align with the hip joints of the user and knee actuators 700 align with the knee joints of the user. A more detailed description of the structural units of exoskeleton 100 is provided below, followed by a more detailed description regarding mechanisms of actuation, control, and use of the exoskeleton.

Figure 2B:
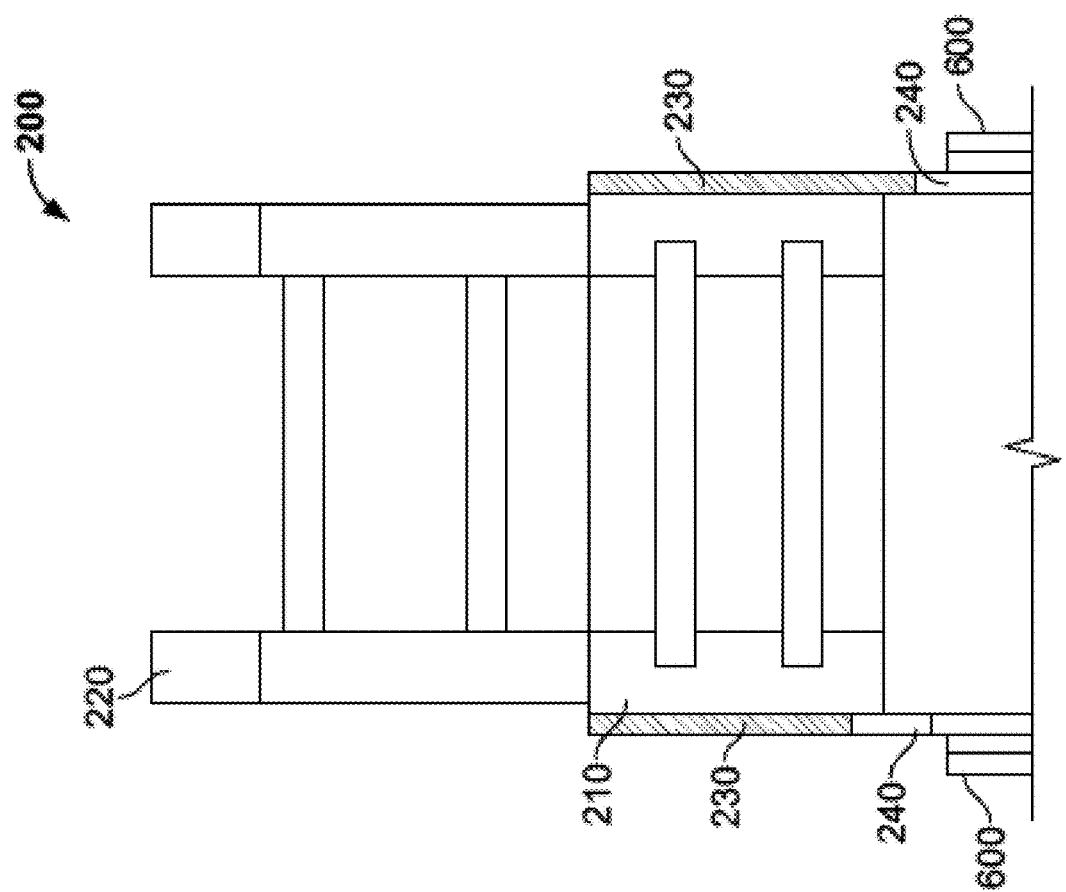
FIG. 2B is an isolated front view of the torso support of FIG. 2A.
Figure 2A:
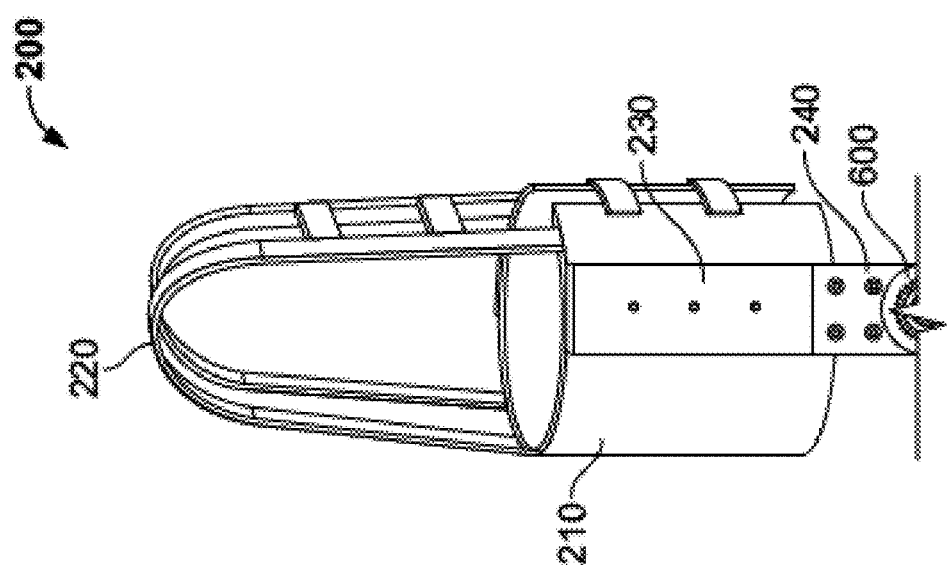
FIG. 2A is an isolated side view of a torso support of the exoskeleton.

Upper extremity portion 200 is shown in side and front views in FIGS. 2A-B, respectively. Upper extremity portion 200 may generally include a torso support 210, torso straps 220, torso panels 230, and upper hip brackets 240.

Torso support 210 may provide support to a user in exoskeleton 100 in order to help keep the user upright or otherwise in a stable position. This support may be provided in part by the rigidity of torso support 210, as well as via a stable connection to the lower extremity section 300 of exoskeleton 100 via torso panels 230. The term "panel," as used herein, refers to a supporting structure, such as the panels illustrated or other supports or struts. Torso support 210 may be formed of any suitable material, but preferably is formed of a lightweight, rigid material such as carbon fiber. Preferably, torso support 210 has one or more surface contours that match or otherwise correspond to a user's torso. With this configuration, torso support 210 may have a relatively low profile compared to another configuration that does not follow the contours, or wrap around, the user's torso. In the illustrated embodiment, torso support 210 is curved and, when positioned on a user's torso, extends completely around the posterior and sides of the torso, with an anterior portion of the torso remaining exposed. Torso support 210 may include padding or other features, particularly on the torso-contacting surfaces, to provide user comfort while maintaining user stability.

Torso support 210 may include a number of straps 220 to facilitate connecting torso support 210 to a user's torso. For example, as shown in FIGS. 2A-B, torso support 210 may include straps 220 in the form of two shoulder straps and one or more horizontal straps extending from one shoulder strap to the other shoulder strap. Torso straps 220 may connect to one another and/or to torso support 210 via any suitable connection mechanism, including buckles, snaps, hook and loop fasteners, and the like. It should further be understood that straps 220 may take any suitable form to facilitate coupling torso support 210 to a user's torso. Some or all of the torso straps 220 may be omitted if torso support 210 provides a stable enough connection to a user's torso.

Figure 2C:
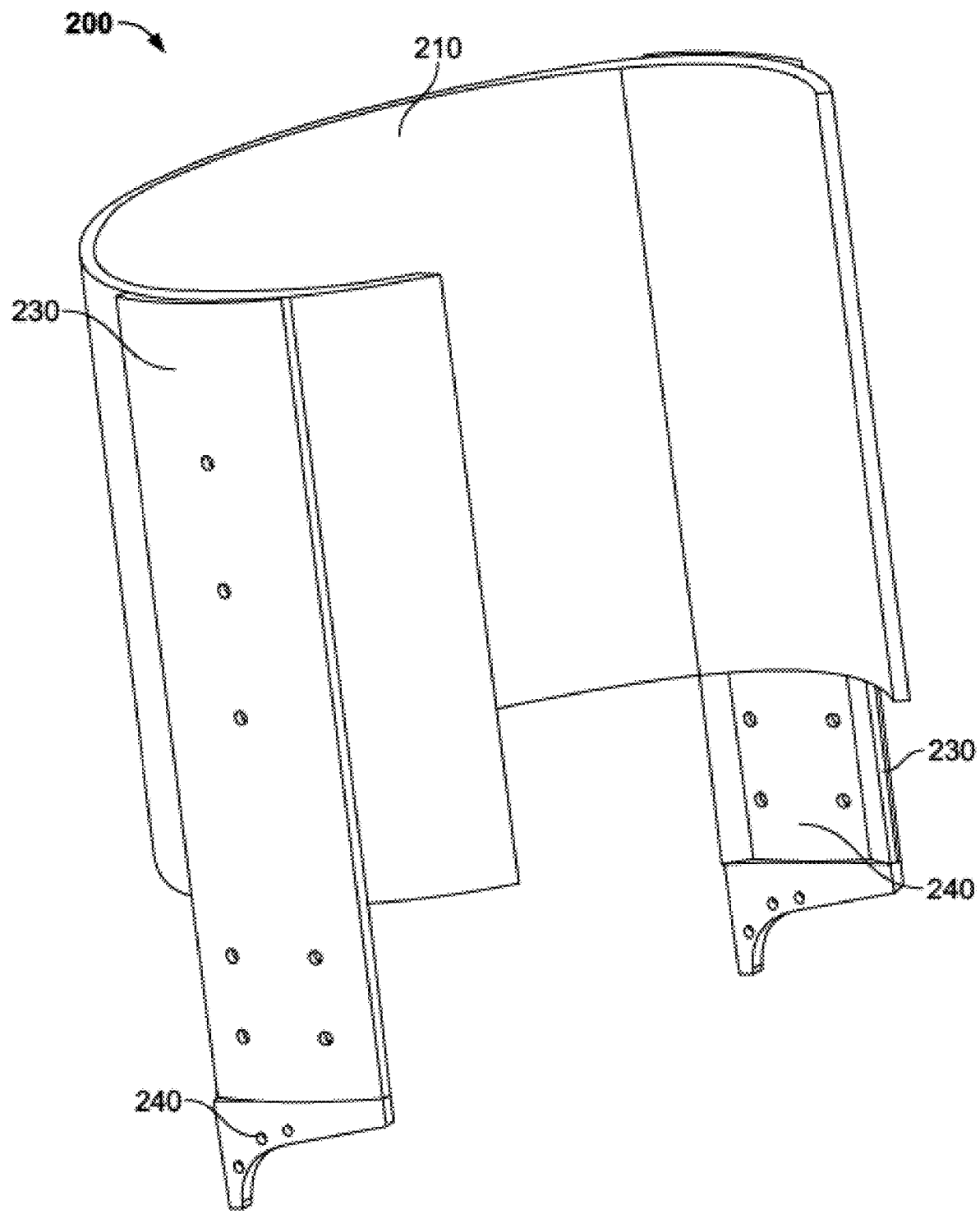
FIG. 2C is an isolated perspective view of the torso support of FIG. 2A.

Torso support 210, torso panels 230, and upper hip brackets 240 are shown in FIG. 2C with the remainder of exoskeleton 100 omitted. Torso panels 230 may be formed of any suitable material, such as carbon fiber, metals or metal alloys including aluminum and steel, plastic, polymers, or combinations thereof. Preferably, an inner surface of each torso panel 230 is curved or otherwise contoured, for example with concave curvature, to match the contour of the outer surface of torso support 210. Similarly, an outer surface of each torso panel 230 is preferably curved or otherwise contoured, for example with a convex curvature, to facilitate upper extremity portion 200 maintaining a relatively low profile. Upper hip brackets 240 may couple torso panels 230 to hip actuators 600. Upper hip brackets 240 may be formed of any suitable rigid material, including carbon fiber, metals and metal alloys including aluminum and steel, plastic, polymers, or combinations thereof. Preferably, an inner surface of each upper hip bracket 240 is curved or otherwise contoured to match the contour of the outer surface of torso panels 230. It should be understood that upper hip bracket 240 may be formed of two parts, including a first inner portion and an outer second portion that collectively flank or "sandwich" the torso panel 230 between the inner and outer portions of the upper hip bracket 240. Splitting upper hip bracket 240 into an inner portion and an outer portion may relieve certain pressures acting on the torso panel 230 due to the fasteners extending through apertures in the torso panel 230. This may, for example, reduce the likelihood of stress cracks or fractures appearing in torso panel 230 at points of contact with fasteners. It should further be understood that the other brackets described herein, for example including lower hip bracket 410, upper knee bracket 430, and lower knee bracket 510, may also take this two part form for similar reasons. Due to the rigid connection between torso support 210 and torso panels 230, the rigid connection between torso panels 230 and hip brackets 240, and the rigid connection between hip brackets 240 and portions of hip actuators 600, any rotation of hip actuators 600 is transferred through the hip brackets 240, the torso panels 230, the torso support 210, and finally to the torso of the user positioned within the upper extremity section 200. Hip actuators 600, including the connection between hip brackets 240 and hip actuators 600, are described in greater detail below in connection with FIGS. 8A-D.

Upper leg section 400 of lower extremity portion 300 is shown in side and front views in FIGS. 3A-B, respectively. Upper leg section 400 may extend from the center of hip actuators 600 to the center of knee actuators 700, and may include lower hip brackets 410, upper leg panel 420, upper knee bracket 430, and one or more straps 440, 450.

Similar to torso support 210 and torso panels 230, upper leg panels 420 and straps 440, 450 may provide support to a user positioned in exoskeleton 100. Upper leg panels 420 may be formed of any suitable material, such as carbon fiber, aluminum, steel, plastic, polymers, or combinations thereof. Also similar to torso panels 230, upper leg panels 420 are preferably contoured to generally match the contours of the user in order to reduce the profile of exoskeleton 100.

Figure 4A:
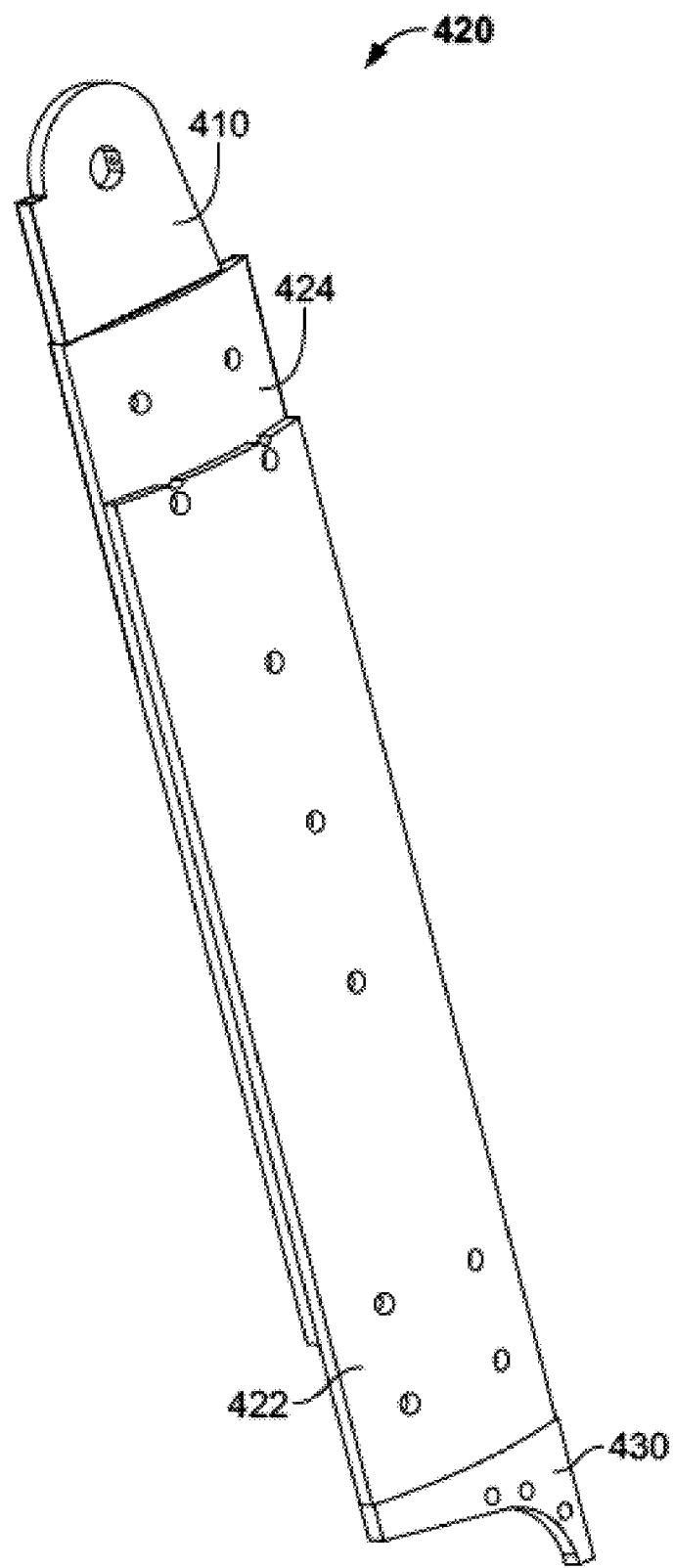
FIG. 4A is a perspective view of an upper leg panel of FIG. 3A.
Figure 4B:
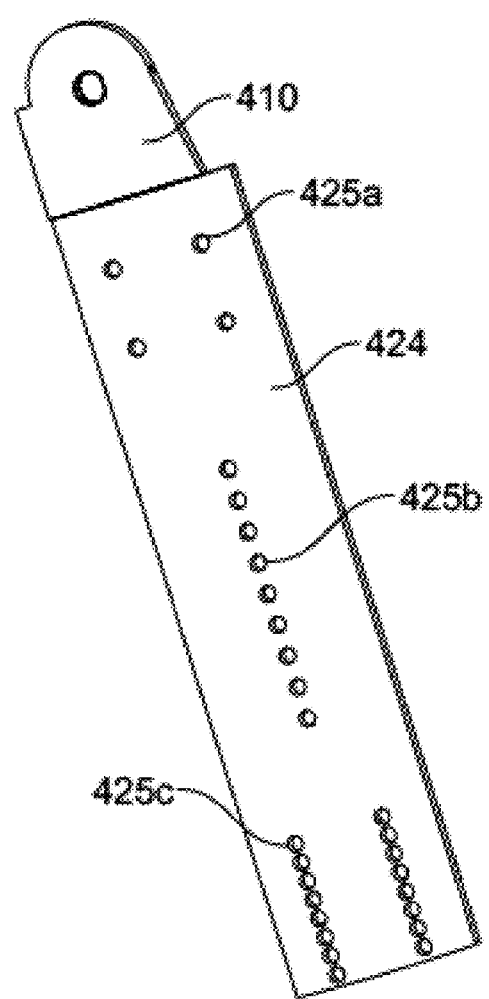
FIGS. 4B-C are perspective views of the outer surfaces of components of the upper leg panel of FIG. 4A.
Figure 4C:
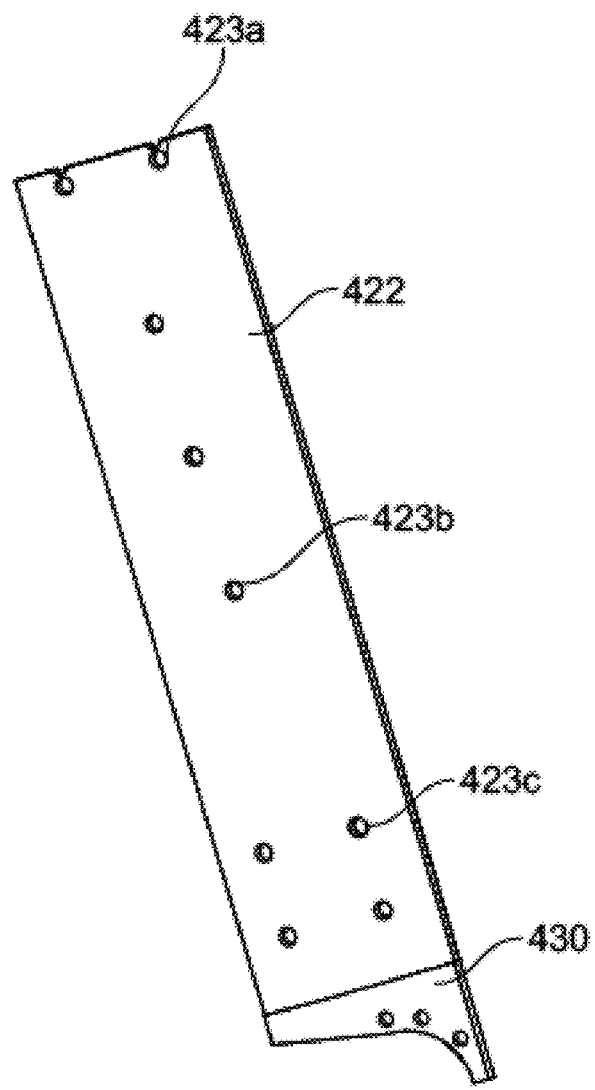
Figure 4D:
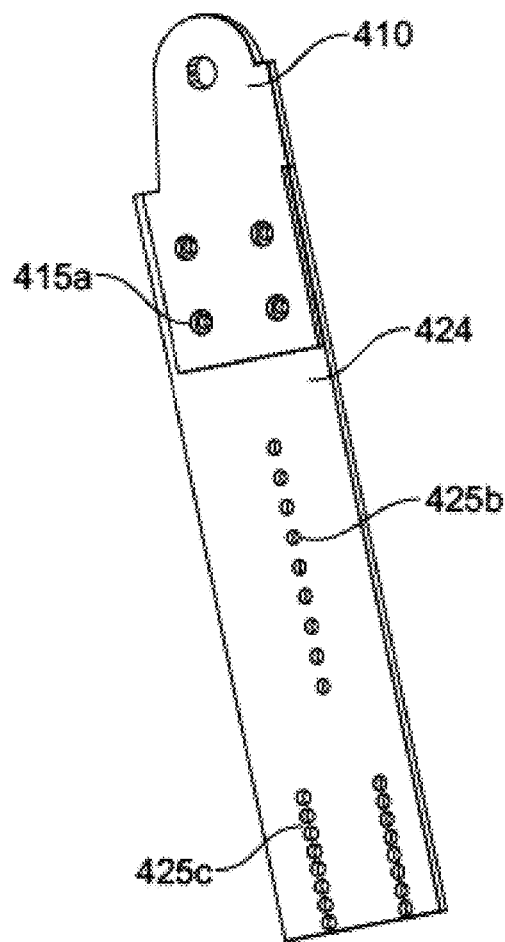
FIGS. 4D-E are perspective views of the inner surfaces of components of the upper leg panel of FIG. 4A.
Figure 4E:
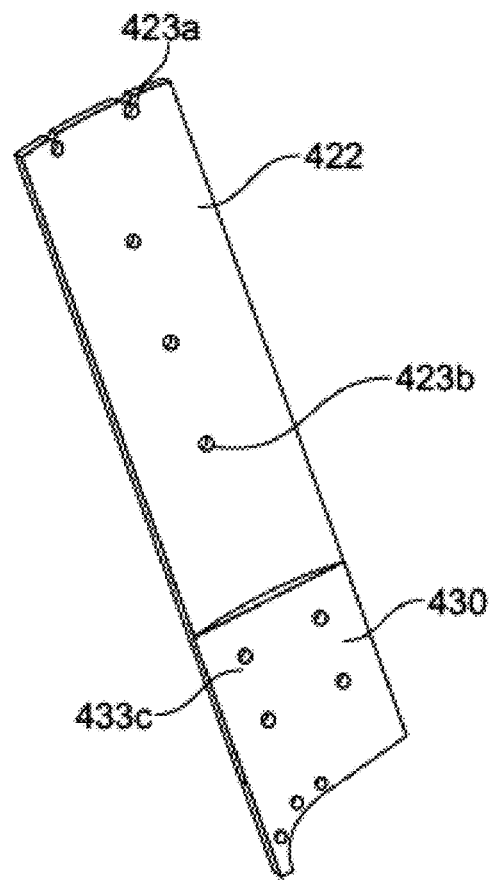

As shown in FIG. 4A, each upper leg panel 420 may include an outer panel 422 and an inner panel 424. Lower hip bracket 410 may be coupled to inner panel 424, and upper knee bracket 430 may be coupled to outer panel 422. The outer surfaces of inner panel 424 and outer panel 422 are shown isolated in FIGS. 4B and 4C, respectively, while the inner surfaces of inner panel 424 and outer panel 422 are shown isolated in FIGS. 4D and 4E, respectively.

Outer panel 422 and inner panel 424 may each include a plurality of apertures or holes extending therethrough to facilitate attachment to one another, to brackets, and to accessory devices such as straps. For example, inner panel 424 may include a first set of apertures 425a on an upper side to facilitate attachment to one or more corresponding apertures 415a of lower hip bracket 410, a second set of vertically arranged apertures 425b to facilitate attachment to outer panel 422, and a third set of apertures 425c to facilitate attachment to one or more corresponding apertures 433c of upper knee bracket 430. Outer panel 422 may include a first set of apertures 423a on an upper side to facilitate coupling to one or more corresponding apertures 415a of lower hip bracket 410, a second set of vertically arranged apertures 423b to facilitate attachment to one or more corresponding apertures 425b of inner panel 424, and a third set of apertures 423c to facilitate attachment to one or more corresponding apertures 433c of upper knee bracket 430.

With the configuration described above, outer panel 422 may be fastened to inner panel 424, via fasteners extending through apertures 423b and 425b, at different vertical positions relative to one another. This provides the ability to increase or decrease the total vertical length of the upper leg panels 420 to suit users of different sizes. Additionally, the configuration allows for lower hip bracket 410 to be sandwiched between inner panel 424 and outer panel 422, with all three being coupled via apertures 423a, 425a, and 415a. Similarly, upper knee bracket 430 may be sandwiched between inner panel 424 and outer panel 422, with all three being coupled via apertures 423c, 425c, and 433c. To the extent any gap spaces exist between inner panel 424 and outer panel 422, those gaps may be filled with spacers, rubber sheeting, or other suitable materials to provide a substantially uniform profile. This may apply to other gap spaces created between other panels described herein.

As should be clear from the figures, both outer panel 422 and inner panel 424 preferably have matching contours that follow the contour of the user to reduce the profile of upper leg panels 420, as described above. For example, an inner surface of each panel 422, 424 may be concave and an outer surface of each panel 422, 424 may be convex. Lower hip bracket 410 and upper knee bracket 430 may include additional apertures and contours, for example with a bottom edge of upper knee bracket 430 being curved, to facilitate connection to and/or movement with respect to the corresponding hip actuator 600 or knee actuator 700, the structure and function of which is described in greater detail below.

Referring once again to FIGS. 3A-B, one or more straps 440, 450 may be connected to upper leg panel 420 in any suitable manner to facilitate securing the user to exoskeleton 100. For example, in the illustrated embodiment, each strap 440, 450 is a loop which may be wrapped around the thigh of the user to connect the upper leg of the user to the upper leg panel 420. The straps 440, 450 may be connected to the upper leg panel 420 in any suitable fashion, including through use of any of the apertures in the upper leg panel 420. The straps may be formed of neoprene, cloth, wires, plastic, rope, gel, foam materials, natural or inorganic compounds, or any combination thereof. Preferably, the straps 440, 450 provide strength while maintaining a low profile and comfort to the user. As with other straps described herein, straps 440, 450 may be fastened via buckles, hook and loop fasteners, or other suitable mechanisms. As shown in FIG. 3A, the straps 440, 450 may take different shapes. For example, strap 440 is shown as being relatively narrow, while strap 450 is shown as being relatively wide, taking a form like a sleeve, which may provide reduced pressure points compared to strap 440.

Figure 5C:
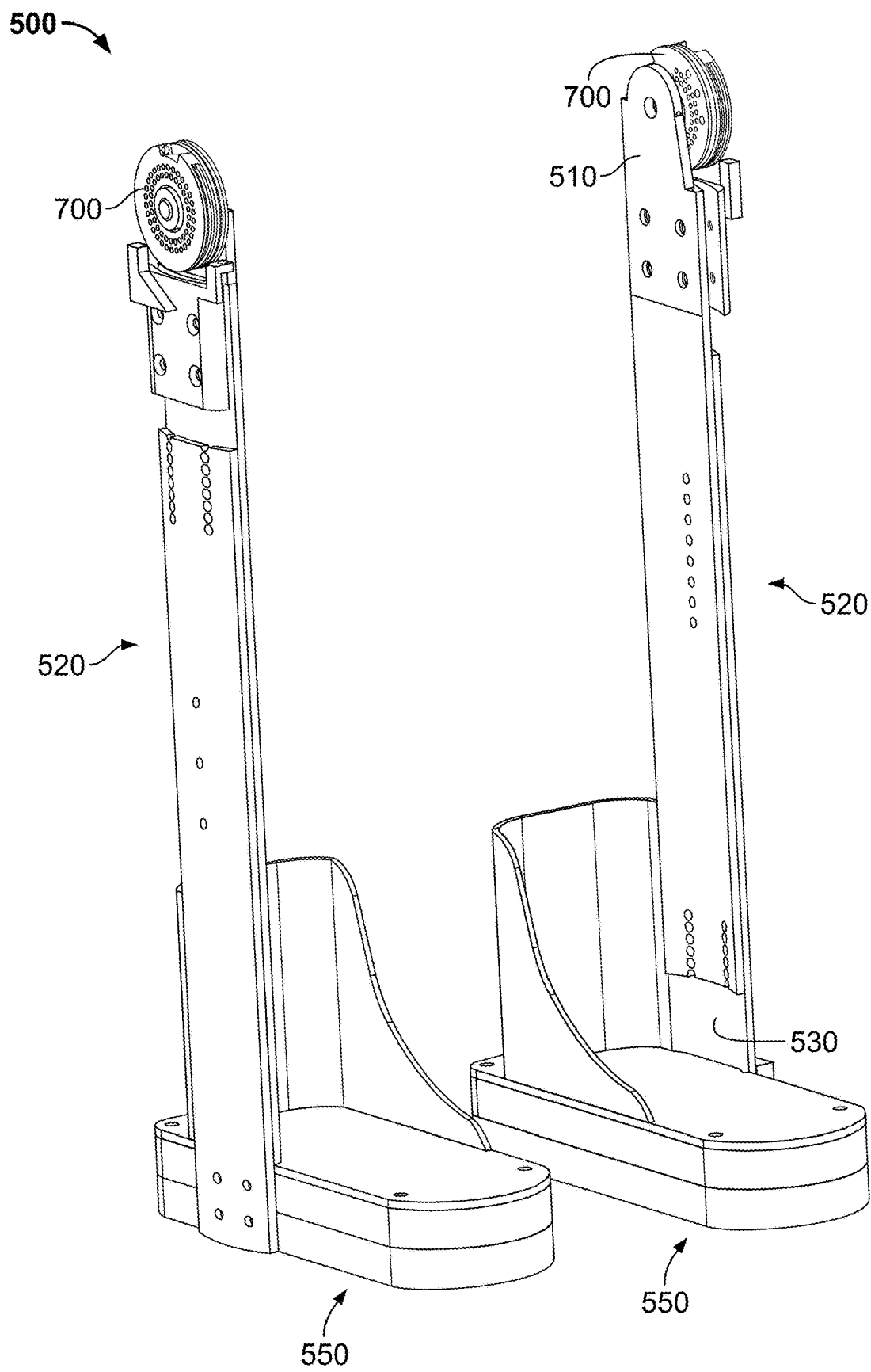
FIG. 5C is an isolated perspective view of the lower leg section of FIG. 5A.

Lower leg section 500 of lower extremity portion 300 is shown in side, front, and perspective views in FIGS. 5A-C, respectively. Lower leg section 500 may extend below the center of knee actuators 700, and may include lower knee brackets 510, lower leg panel 520, foot bracket 530, one or more straps 540 (not shown in FIG. 5C), and foot module 550.

Similar to upper leg panels 420 and straps 440, 450, lower leg panels 520, straps 540, and foot module 550 may provide support to a user positioned in exoskeleton 100. Lower leg panels 520 may be formed of any suitable material, such as carbon fiber, aluminum, steel, plastic, polymers, or combinations thereof. Also similar to upper leg panels 420, lower leg panels 520 are preferably contoured to generally match the contours of the user in order to reduce the profile of exoskeleton 100.

Figure 6A:
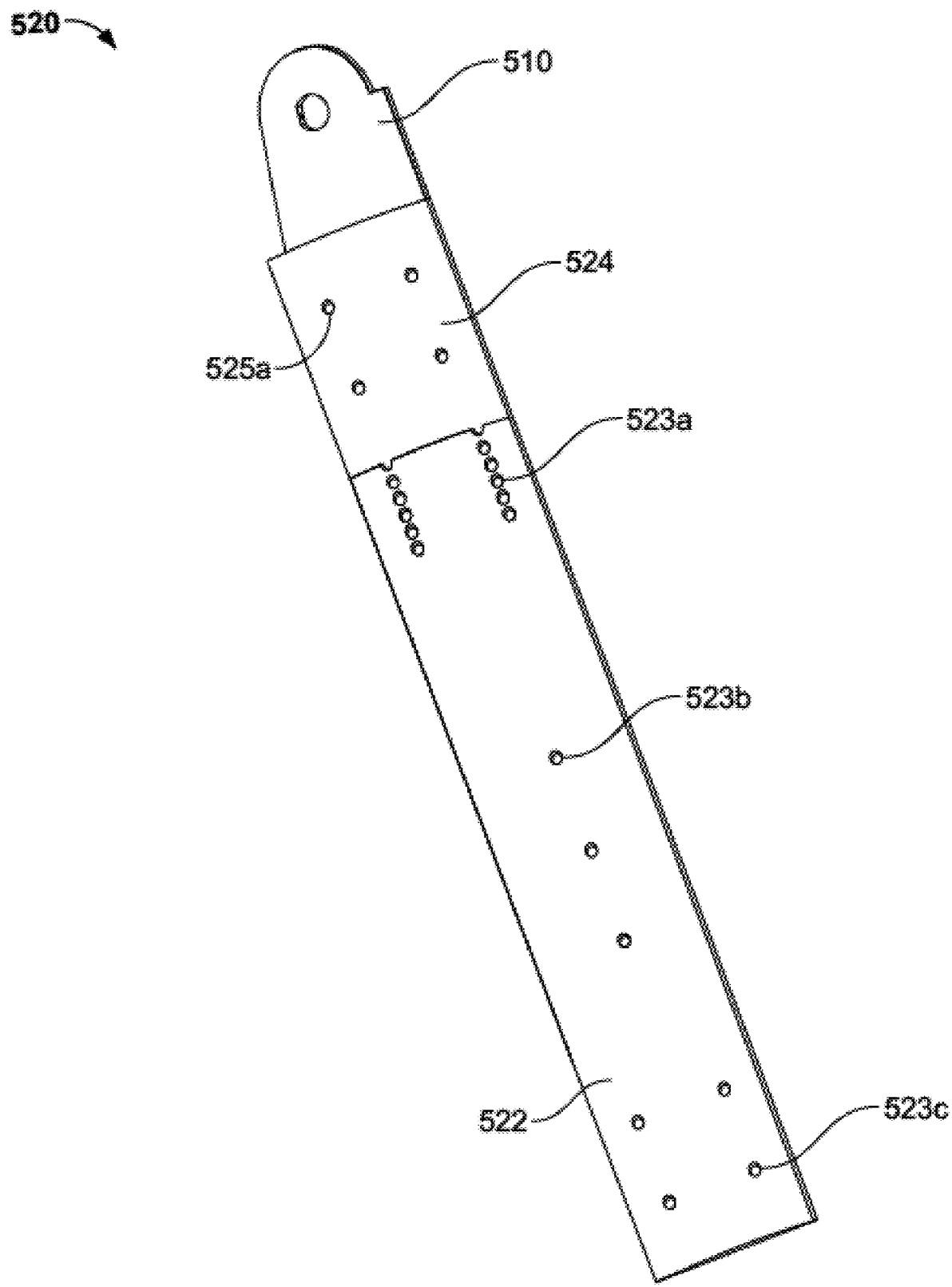
FIG. 6A is a perspective view of a lower leg panel of FIG. 5A.
Figures 6D, 6E:
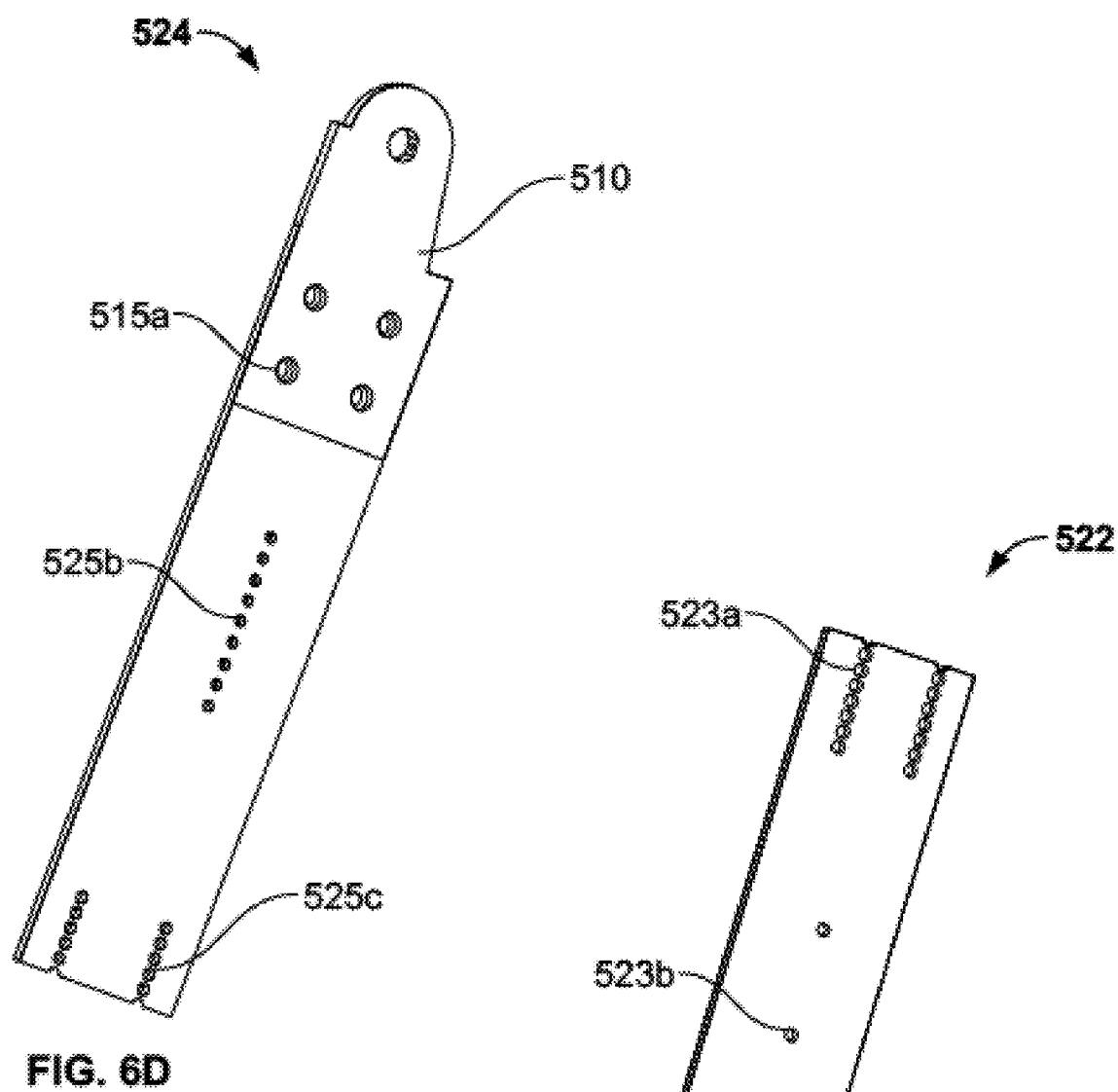
FIGS. 6D-E are perspective views of the inner surfaces of components of the lower leg panel of FIG. 6A.

As shown in FIG. 6A, each lower leg panel 520 may include an outer panel 522 and an inner panel 524. Lower knee bracket 510 may be coupled to inner panel 524, and foot bracket 530 may be coupled to outer panel 522. The outer surfaces of inner panel 524 and outer panel 522 are shown isolated in FIGS. 6B and 6C, respectively, while the inner surfaces of inner panel 524 and outer panel 522 are shown isolated in FIGS. 6D and 6E, respectively.

Outer panel 522 and inner panel 524 may each include a plurality of apertures or holes extending therethrough to facilitate attachment to one another, to brackets, and to accessory devices such as straps. For example, inner panel 524 may include a first set of apertures 525a on an upper side to facilitate attachment to one or more corresponding apertures 515a of lower knee bracket 510, a second set of vertically arranged apertures 525b to facilitate attachment to outer panel 522, and a third set of apertures 525c to facilitate attachment to one or more corresponding apertures 533c of foot bracket 530. Outer panel 522 may include a first set of apertures 523a on an upper side to facilitate coupling to one or more corresponding apertures 515a of lower knee bracket 510, a second set of vertically arranged apertures 523b to facilitate attachment to one or more corresponding apertures 525b of inner panel 524, and a third set of apertures 523c to facilitate attachment to one or more corresponding apertures 533c of foot bracket 530.

With the configuration described above, outer panel 522 may be fastened to inner panel 524, via fasteners extending through apertures 523b and 525b, at different vertical positions relative to one another. This provides the ability to increase or decrease the total vertical length of the lower leg panels 520 to suit users of different sizes. Additionally, the configuration allows for lower knee bracket 510 to be sandwiched between inner panel 524 and outer panel 522, with all three being coupled via apertures 523a, 525a, and 515a. Similarly, foot bracket 530 may be sandwiched between inner panel 524 and outer panel 522, with all three being coupled via apertures 523c, 525c, and 533c. Foot module 550 may be provided with multiple slots and/or screw holes in the posterior to anterior direction (i.e. from the heel to the toe) to provide for a plurality of attachment locations of the lower leg panels 520 to the foot module, providing for additional adjustability of the exoskeleton 100.

Similar to upper leg panels 420, both outer panel 522 and inner panel 524 of lower leg panels 520 preferably have matching contours that follow the contour of the user to reduce the profile of upper leg panels 520. For example, an inner surface of each panel 522, 524 may be concave and an outer surface of each panel 522, 524 may be convex. Lower knee bracket 510 and foot bracket 530 may include additional apertures and contours to facilitate connection to knee actuator 700 or foot module 550, the structure and function of which is described in greater detail below.

Referring once again to FIGS. 5A-C, one or more straps 540 may be connected to lower leg panel 520 in any suitable manner to facilitate securing the user to exoskeleton 100. For example, in the illustrated embodiment, strap 540 is a loop which may be wrapped around the lower leg below the knee, or alternately above, on, or below the calf, of the user to connect the lower leg of the user to the lower leg panel 520. The strap 540 may be connected to the lower leg panel 520 in any desired fashion, including through use of any of the apertures in the lower leg panel 520. The straps may be formed of neoprene, cloth, wires, plastic, rope, gel, foam materials, natural or inorganic compounds, or any combination thereof. Preferably, the strap 540 provides strength while maintaining a low profile and comfort to the user. As with other straps described herein, strap 540 may be fastened via buckles, hook and loop fasteners, or other suitable mechanisms. Additional straps may be included with the foot module 550, which is described in greater detail below.

Figure 7:
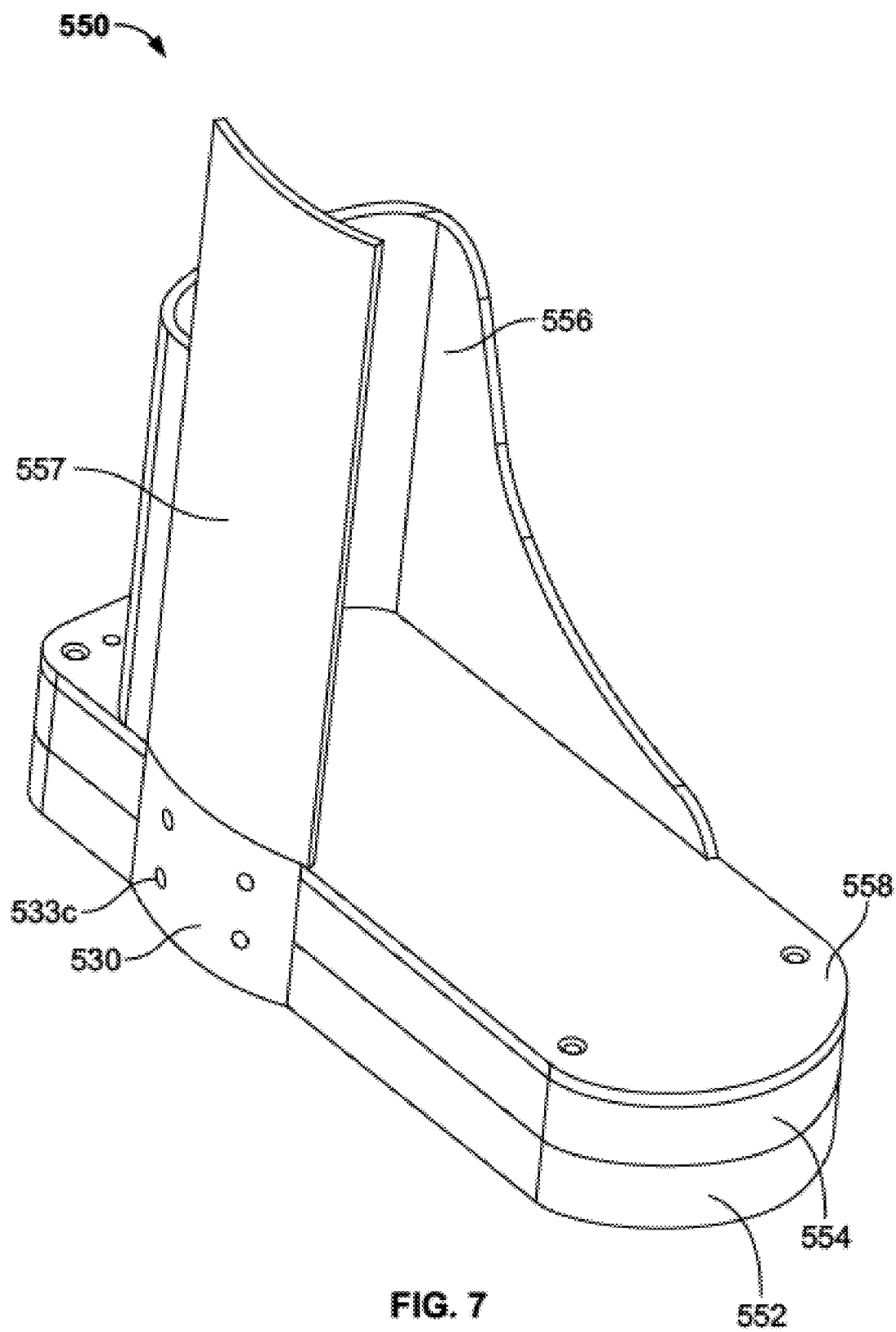
FIG. 7 is an isolated perspective view of a foot module of the lower leg section of FIG. 5A.

Foot module 550 is shown in greater detail in FIG. 7. While FIG. 7 illustrates foot module 550 corresponding to the right foot of a user, it should be understood that another foot module 550 with identical components, for example positioned in a mirrored configuration, may be used with exoskeleton 100. Generally, foot module 550 may include a lower platform 552, and upper platform 554, an ankle support 556, and ankle panel 557. Lower platform 552 may serve as the ground-contacting portion of foot module 550, while upper platform 554 may provide a support surface for the user's foot as well as acting as a guard to protect the user's foot from cables and other actuation mechanisms positioned within or near foot module 550. Rubber or other suitable material may be added to the bottom of lower platform 552 to assist in traction and to house one or more sensors, described in greater detail below. A sole 558 may be positioned on top of upper platform 554, to provide cushioning and/or sensing functionality. In addition, lower platform 552 and upper platform 554 may together define an internal compartment in which control mechanisms of the exoskeleton 100 are positioned. As is described in greater detail below, the positioning of control mechanisms in a compartment within foot module 550 underneath the user's foot may reduce or eliminate the need to have bulky and/or conspicuous control system housings, such as wearable backpacks. These control mechanisms may include the mechanical actuator systems that drive hip actuators 600 and knee actuators 700, as well as electronic control systems including processor unit(s), power unit(s), sensors, and the like. Upper platform 554 and lower platform 552 may be formed of, for example, aluminum, steel, plastic, wood, composites, resins, or combinations thereof. Sole 558 may be a membrane layer formed of a material such as cloth, polymers, leather, neoprene, organic or inorganic rubber, foam, gel, or other suitable materials. Sole 558 may be angled slightly forward, such that the posterior portion of sole 558 is positioned farther from the ground-contacting surface of lower platform 552 than the anterior portion of sole 558. The forward angle may additionally or alternately be applied to the bottom of lower platform 552. This forward angle may facilitate a user in exoskeleton 100 initiate a step. In addition, sole 558 may include sensors which may, for example, register weight transfer, determine the location of portions of exoskeleton 100, compute heart rate, temperature, perspiration and the like. These sensors are described in greater detail below.

Foot bracket 530 may be coupled to lower platform 552 and/or upper platform 554 via fasteners extending through apertures 533c, the fasteners also extending through lower leg panel 520, ultimately coupling foot module 550 to lower panel 520. Although an outer surface of foot bracket 530 may be convex, an inner surface may be substantially planar so that it is flush with the planar side surfaces of lower platform 552 and upper platform 554. It should be understood that foot bracket 530 may actually comprise two separate similarly shaped brackets, which may allow a shock-absorbing material such as rubber to be sandwiched between the two foot brackets to reduce vibrations or other unwanted energy from being transmitted from foot module 550 to the remainder of exoskeleton 100. It should be understood that such a shock-absorbing material may be used between any or all other joint brackets described herein to provide the same or similar dampening and/or protective action. Ankle support 556 may be coupled to upper platform 554 and/or lower platform 552. Ankle support 556 may extend substantially orthogonal to an upper surface of upper platform 554, with a rear portion of ankle support 556 extending a first distance, and the side surfaces of ankle support 556 tapering to a smaller distance in the anterior direction. With this configuration, ankle support 556 generally follows the contours of the ankle and foot, providing support and/or protection to the user. In addition, ankle support 556 may include an ankle panel 557 having a convex outer surface and a concave inner surface. The outer surface of ankle panel 557 may be flush with an inner surface of lower leg panel 520, with the inner surface of ankle panel 557 generally conforming to the shape of the user's lower leg. Ankle panel 557 may serve as a barrier between lower leg panel 520 and the user's lower leg, protecting the lower leg from cables or other moving components (described in greater detail below) coupled to foot module 550. In addition, ankle panel 557 may include padding or other material to enhance the user's comfort, similar to padding described above in relation to torso support 210. It should be understood that any or all of the panels described herein may include similar padding. Ankle panel 557 may be formed as an integral part with ankle support 556, but the structures may alternatively be separate. In addition, ankle panel 557 may contain apertures or other structures to facilitate fastening of ankle panel 557 to one or both lower leg panels 520, although such fastening is not required.

As should be clear from the above description, exoskeleton 100 may include two similar leg supports, which may have components oriented in mirror image, to facilitate movement of both legs of the user in the exoskeleton 100, although an exoskeleton 100 with a single leg support may be possible. As noted above, each leg support includes a hip actuator 600 to facilitate movement of upper extremity portion 200 relative to upper leg section 400, and a knee actuator 700 to facilitate movement of upper leg section 400 relative to lower leg section 500.

Figure 8A:
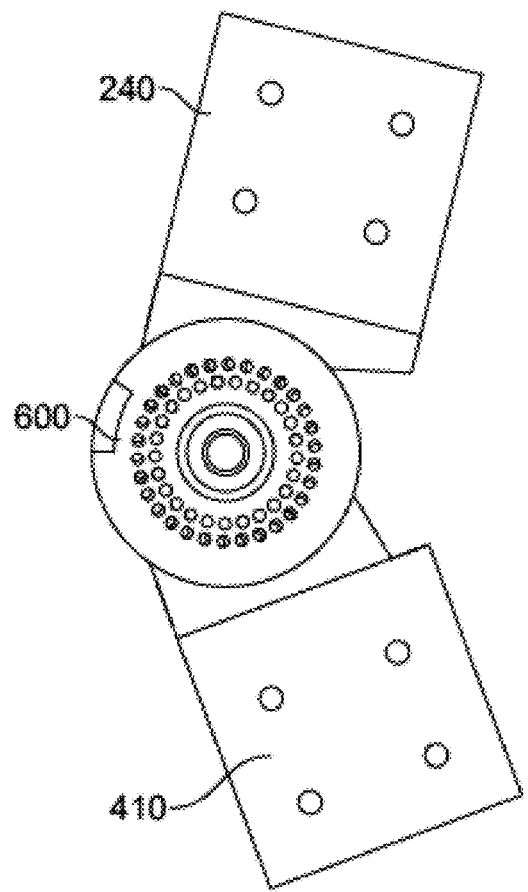
FIGS. 8A-C are isolated side and perspective views of a hip joint of the exoskeleton.
Figure 8B:
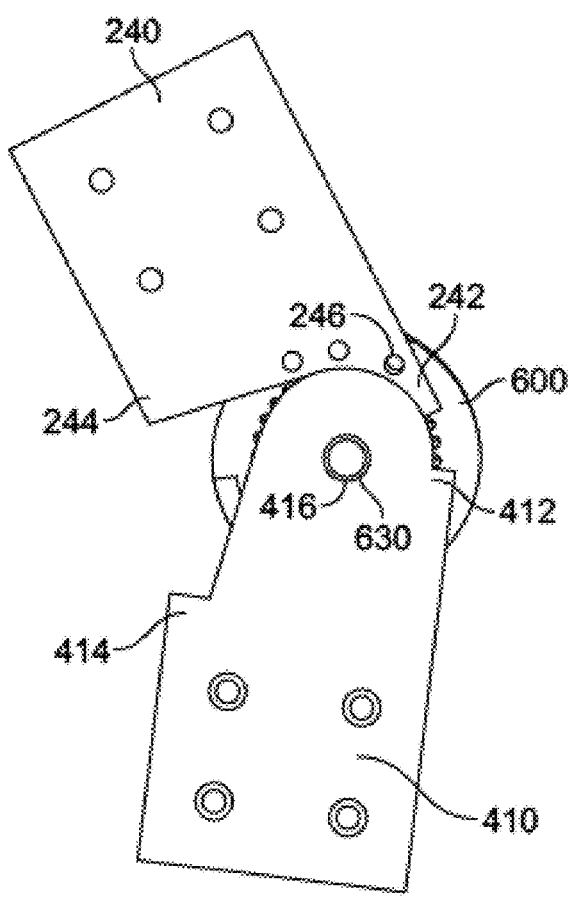
Figure 8C:
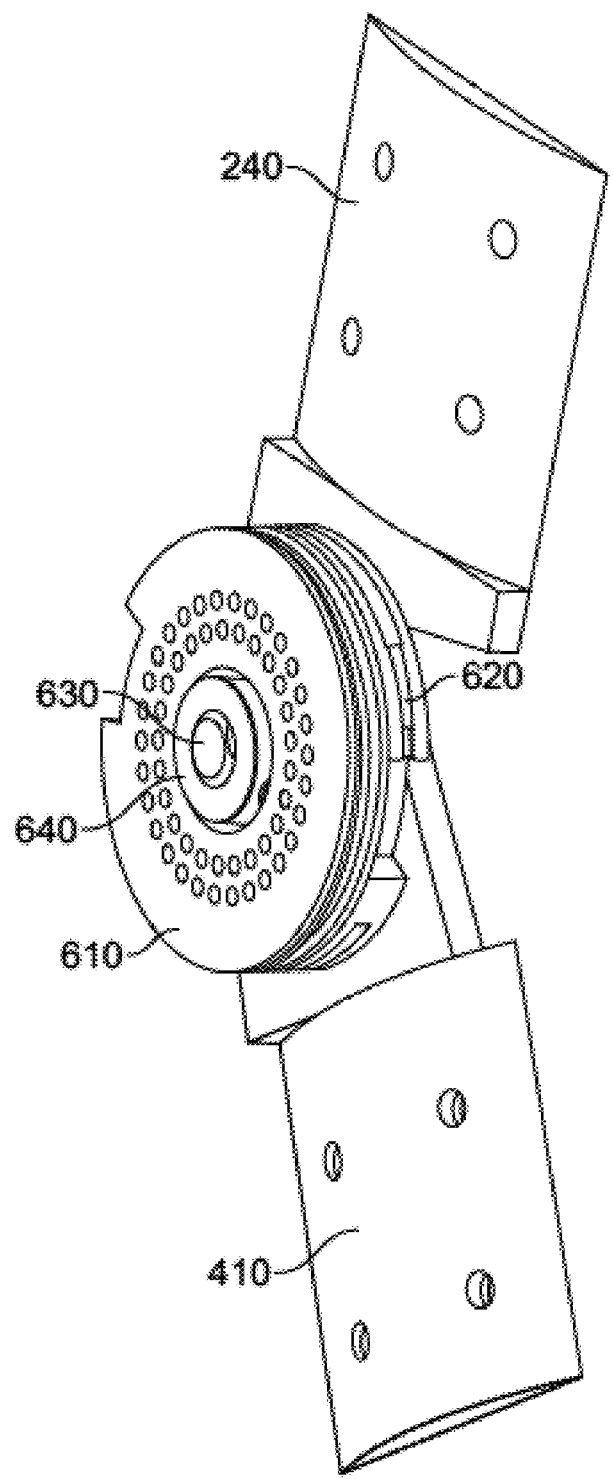
Figure 8D:
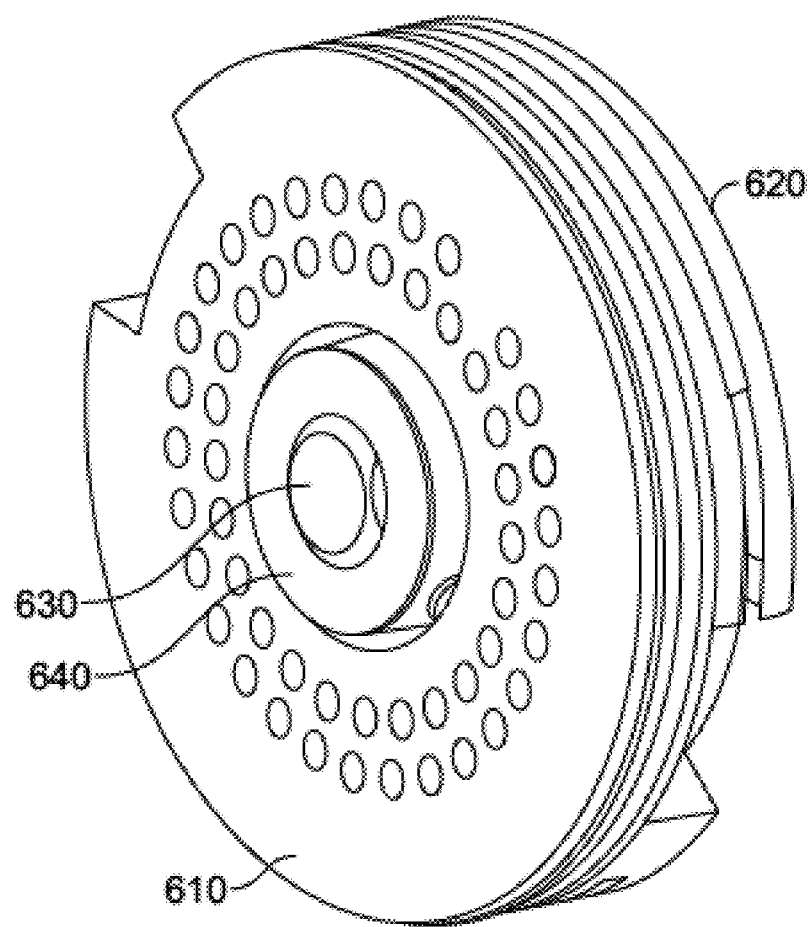
FIG. 8D is an isolated perspective view of an extension spindle and flexion spindle of the hip joint.

The structure of hip actuator 600 and its connection to upper hip bracket 240 and lower hip bracket 410 is shown in greater detail in FIGS. 8A-D. FIGS. 8A-B show side views of hip actuator 600 coupled to upper hip bracket 240 and lower hip bracket 410, with torso panel 230 and upper leg panel 420 omitted for clarity. As best seen in FIGS. 8C-D, hip actuator 600 may include an extension spindle 610, a flexion spindle 620, an axle 630, and a shaft collar 640. One or more bearings may be included, for example by press-fitting, on the interior of the spindle(s). Extension spindle 610 and flexion spindle 620 may each include a plurality of apertures or through holes to facilitate coupling of the spindles to one another and/or to other structures of exoskeleton 100. In the illustrated embodiment, each spindle 610, 620 includes two staggered rows of circumferentially oriented apertures, although other configurations may be suitable. Each spindle 610, 620 may be formed of any suitable material, including any alloy of aluminum, steel, iron, brass, zinc, plastics, composites, and the like.

Referring now to FIGS. 8A-D, a bottom edge of upper hip bracket 240 may include a contoured surface flanked by an extension limiting projection 242 on one side and a flexion limiting portion 244 on the opposite side. Upper hip bracket 240 may also include a plurality of through holes or aperture 246 configured to align with corresponding apertures on extension spindle 610 and flexion spindle 620. One or more fasteners may couple upper hip bracket 240 to extension spindle 610 and flexion spindle 620. A top edge of lower hip bracket 410 may include a contoured surface flanked by an extension limiting surface 412 on one side and flexion limiting surface 414 on the opposite side. Lower hip bracket 410 may also include a through hole or aperture 416 configured to align with a corresponding central apertures of extension spindle 610 and flexion spindle 620. Axle 630 of hip actuator 600 may rotatably couple extension spindle 610 and flexion spindle 620 to lower hip bracket 410 by way of aperture 416, with shaft collar 640 positioned around axle 630 to facilitate rotation of extension spindle 610 and flexion spindle 620 about axle 630. As should be clear from the above description, as extension spindle 610 rotates about the axis of axle 630, flexion spindle 620 and upper hip bracket 240 also rotate along with extension spindle 610, relative to lower hip bracket 410, due to their fixed connections to one another. This rotation may continue, with the contoured edges of the upper hip bracket 240 and lower hip bracket 410 facilitating the rotation, until extension limiting projection 242 of upper hip bracket 240 comes into contact with extension limiting surface 412 of lower hip bracket 410. The contact between these surfaces of the upper hip bracket 240 and lower hip bracket 410 define a maximum extension provided by hip actuator 600. Similarly, as flexion spindle 620 rotates, extension spindle 610 and upper hip bracket 240 also rotate along with flexion spindle 620, relative to lower hip bracket 410. This rotation may continue until flexion limiting portion 244 of upper hip bracket 240 comes into contact with flexion limiting surface 414 of lower hip bracket 410. The contact between these surfaces of the upper hip bracket 240 and lower hip bracket 410 define a maximum flexion provided by hip actuator 600. Although the range of flexion and extension may be varied by, for example, changing the positions of the flexion and extension limiting surfaces of the upper hip bracket 240 and lower hip bracket 410, the illustrated embodiment provides for a maximum of about 90 degrees of rotation from maximum extension to maximum flexion. The mechanisms that drive the rotation of extension spindle 610 and flexion spindle 620 are described in greater detail below. It should be understood that the limits on maximum tension and flexion may be provided as safety features to avoid injuries from overextension and underextension. Rubber surfaces may also be provided at points of contact of the lower hip bracket 410 with the upper hip bracket 240 to function as a shock absorbing layer when maximum extension or flexion is reached.

Additional or alternative mechanisms may be used as safety mechanisms in case exoskeleton 100 loses power or encounters other failure. For example, a linear hydraulic actuator may connect upper hip bracket 240 to lower hip bracket 410 so that, for example following loss of power or other failure, upper hip bracket 240 cannot effectively freely rotate with respect to lower hip bracket 410 in a free-fall motion. Rather, the linear hydraulic actuator connecting the upper hip bracket 240 to the lower hip bracket 410 will provide resistance, causing a relatively slow flexion about actuator 600. Other types of safety systems, including ratchet and pawl type connectors, may be used for similar purposes. For example, a ratchet and pawl connection between upper hip bracket 240 and lower hip bracket 410 may assist hip actuator 600 in coming to a rest position in the case of failure. Similar safety systems may be implemented with respect to other joints described herein.

Figure 9A:
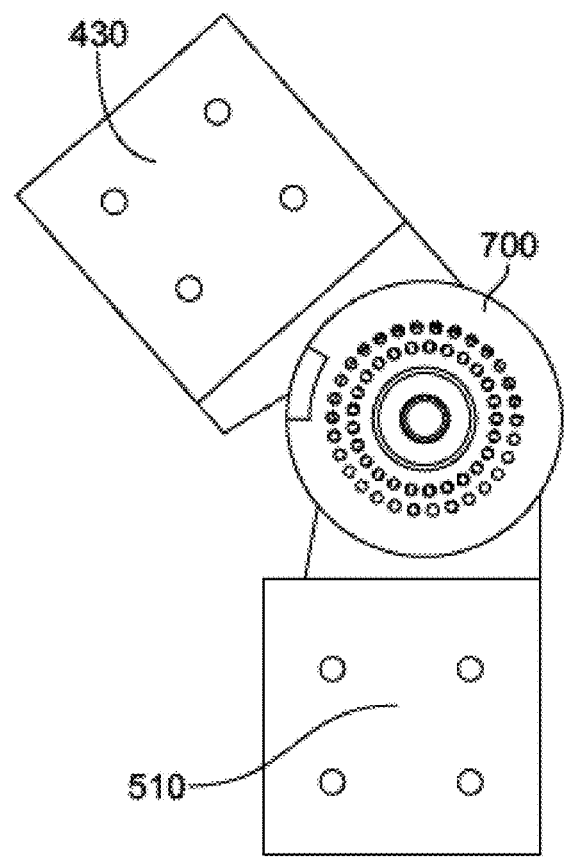
FIGS. 9A-C are isolated side and perspective views of a knee joint of the exoskeleton.
Figure 9B:
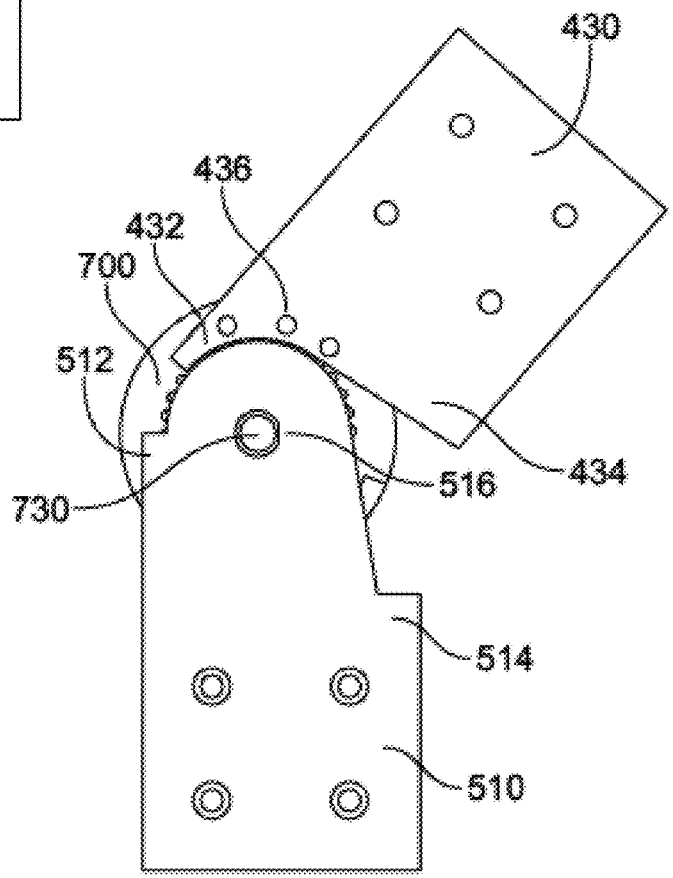
Figure 9C:
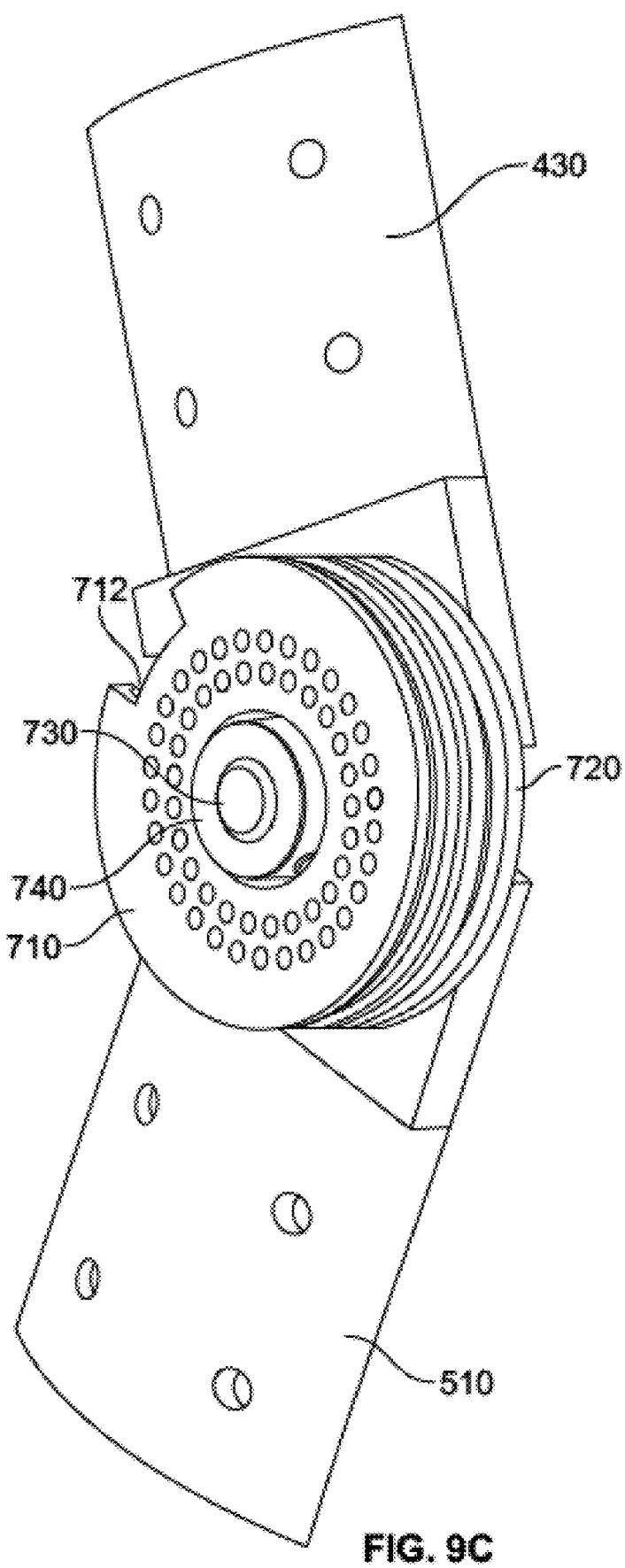

The structure of knee actuator 700 and its connection to upper knee bracket 430 and lower knee bracket 510 is shown in greater detail in FIGS. 9A-C. The relationship between knee actuator 700, upper knee bracket 420, and lower knee bracket 510 may be very similar to the relationship between hip actuator 600, upper hip bracket 240, and lower hip bracket 410, with one main exception. This exception is that the direction of rotation is reversed when moving from extension to flexion. For example, for the right leg structure of the exoskeleton 100 illustrated in FIGS. 8A-D, movement from flexion to extension corresponds to counterclockwise movement of upper hip bracket 240 relative to lower hip bracket 410 in the view shown in FIG. 8A. On the other hand, movement from flexion to extension for the knee actuator 700 corresponds to clockwise movement of upper knee bracket 430 relative to lower knee bracket 510 in the corresponding view shown in FIG. 9A. With the above in mind, the structure of knee actuator 700 and its connection to upper knee bracket 430 and lower knee bracket 510 are described below.

FIGS. 9A-B show side views of knee actuator 700 (which may be substantially similar to hip actuator 600) coupled to upper knee bracket 430 and lower knee bracket 510, with upper leg panel 420 and lower leg panel 520 omitted for clarity. As best seen in FIG. 8C, knee actuator 700 includes a flexion spindle 710, an extension spindle 720, an axle 730, and a collar shaft 740. The components of knee actuator 700 function in the same fashion described in relation to hip actuator 600, with the exception that the outside spindle is a flexion spindle 710 for the knee actuator 700, whereas the outside spindle is an extension spindle 610 in the hip actuator 600.

A bottom edge of upper knee bracket 430 may include a contoured edge flanked by an extension limiting projection 432 on one side and a flexion limiting portion 434 on the opposite side. Upper knee bracket 430 may also include a plurality of through holes or aperture 436 configured to align with corresponding apertures on flexion spindle 710 and extension spindle 720. One or more fasteners may couple upper knee bracket 430 to flexion spindle 710 and extension spindle 720. A top edge of lower knee bracket 510 may include a contoured surface flanked by an extension limiting surface 512 on one side and flexion limiting surface 514 on the opposite side. Lower knee bracket 510 may also include a through hole or aperture 516 configured to align with a corresponding central apertures of flexion spindle 710 and extension spindle 720. Axle 730 of hip actuator 700 may rotatably couple flexion spindle 710 and extension spindle 720 to lower knee bracket 510 by way of aperture 516, with collar shaft 740 positioned around axle 730 to facilitate rotation of flexion spindle 710 and extension spindle 720 about axle 730. As should be clear from the above description, as extension spindle 720 rotates, flexion spindle 710 and upper knee bracket 430 also rotate along with extension spindle 720, relative to lower knee bracket 510, due to their fixed connections to one another. This rotation may continue until extension limiting projection 432 of upper knee bracket 430 comes into contact with extension limiting surface 512 of lower knee bracket 510. Similarly, as flexion spindle 710 rotates, extension spindle 720 and upper knee bracket 430 also rotate along with flexion spindle 710, relative to lower hip bracket 510. This rotation may continue until flexion limiting portion 434 of upper knee bracket 430 comes into contact with flexion limiting surface 514 of lower knee bracket 510. Although the range of flexion and extension may be varied by, for example, changing the positions of the flexion and extension limiting surfaces of the upper knee bracket 430 and lower knee bracket 510, the illustrated embodiment provides for a maximum of about 90 degrees of rotation from maximum extension to maximum flexion. The mechanisms that drive the rotation of extension spindle 720 and flexion spindle 710 are described in greater detail below. As with the hip joint described above, safety mechanisms including shock absorbing layers of material may be provided to absorb energy upon reaching maximum flexion or extension.

Figure 10A:
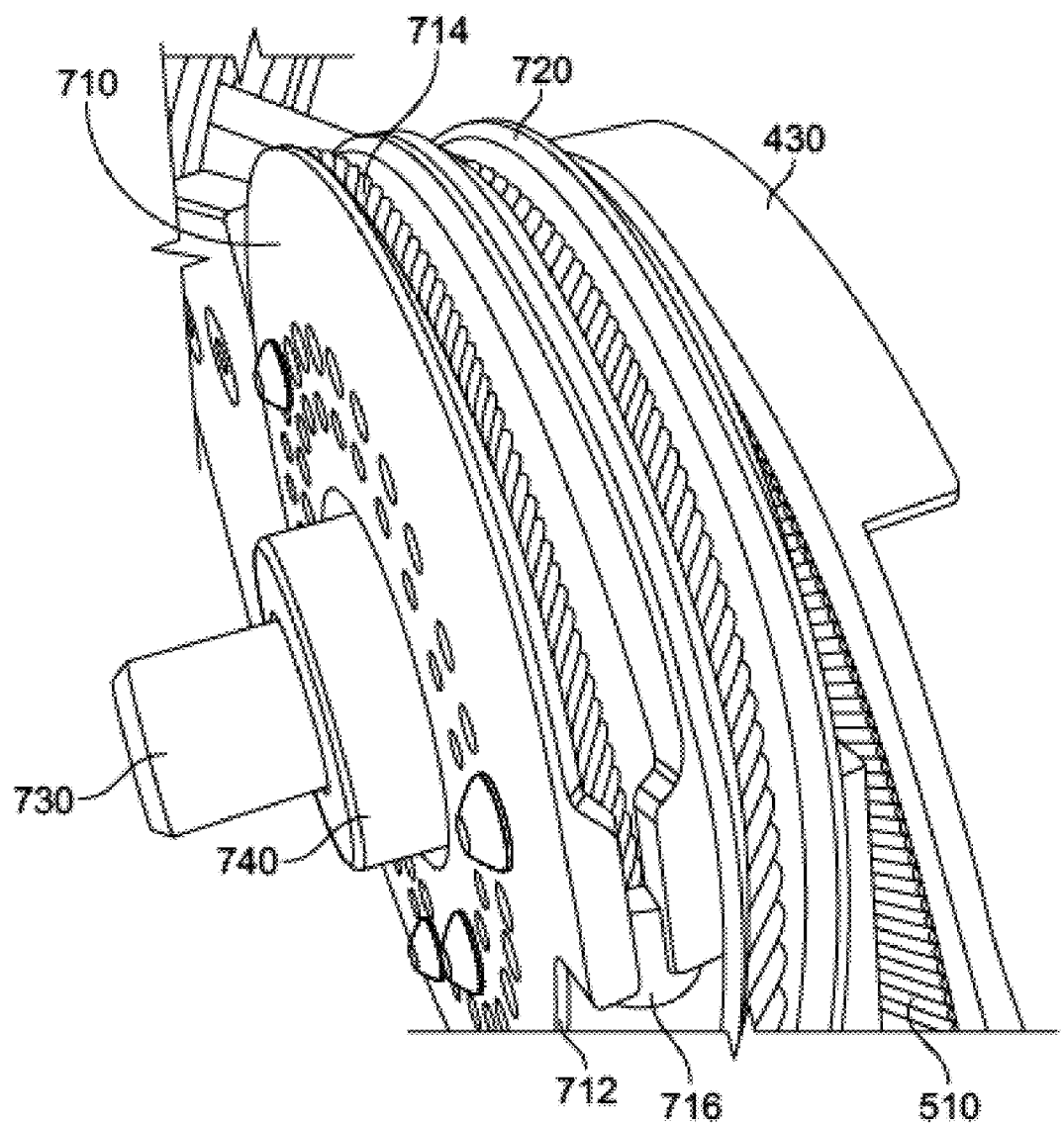
FIG. 10A is a perspective view of an extension spindle and flexion spindle of the knee joint with attached cables.
Figure 10B:
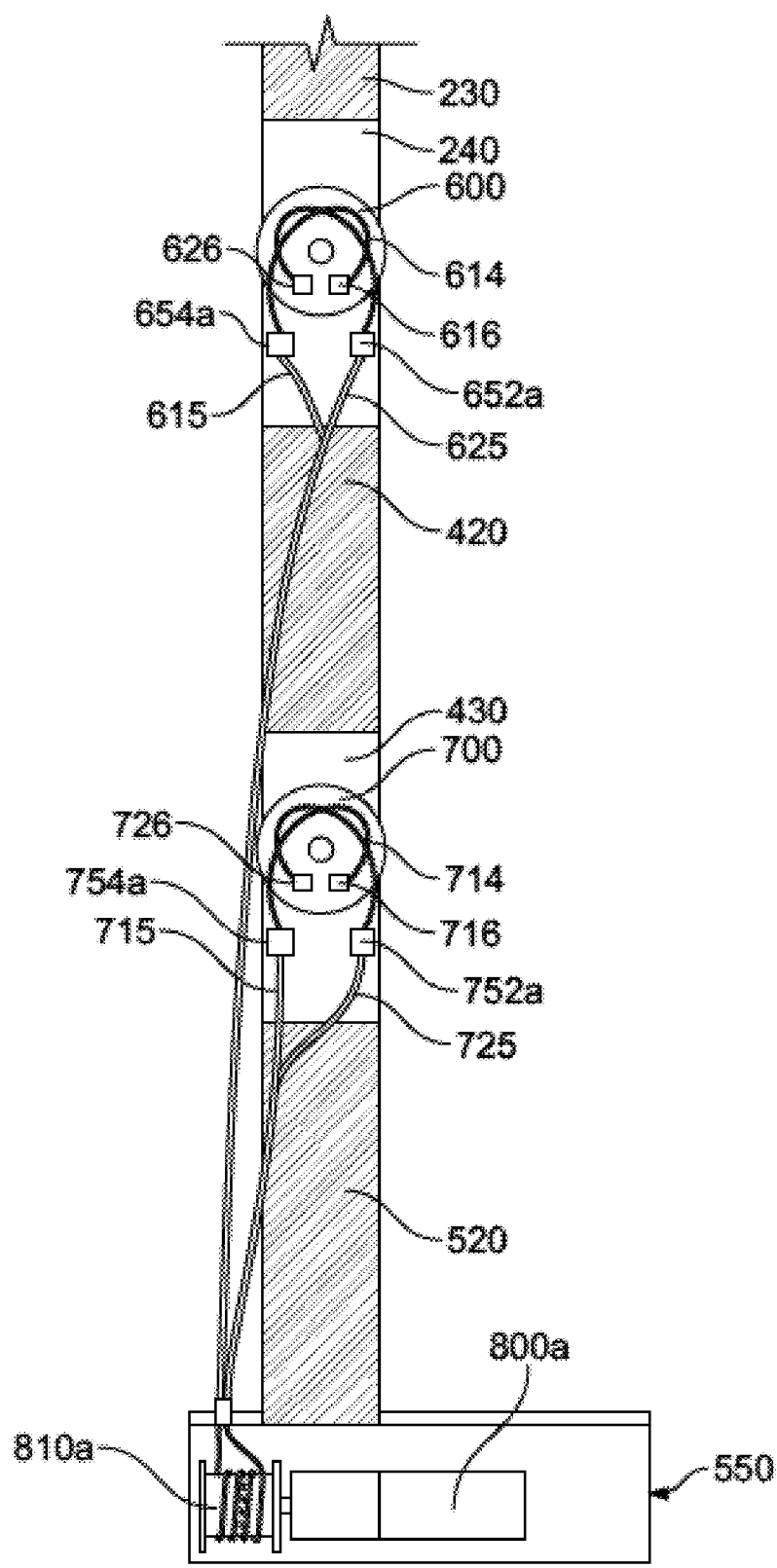
FIG. 10B is a diagrammatic view of cables routed along the exoskeleton.
Figure 10C:
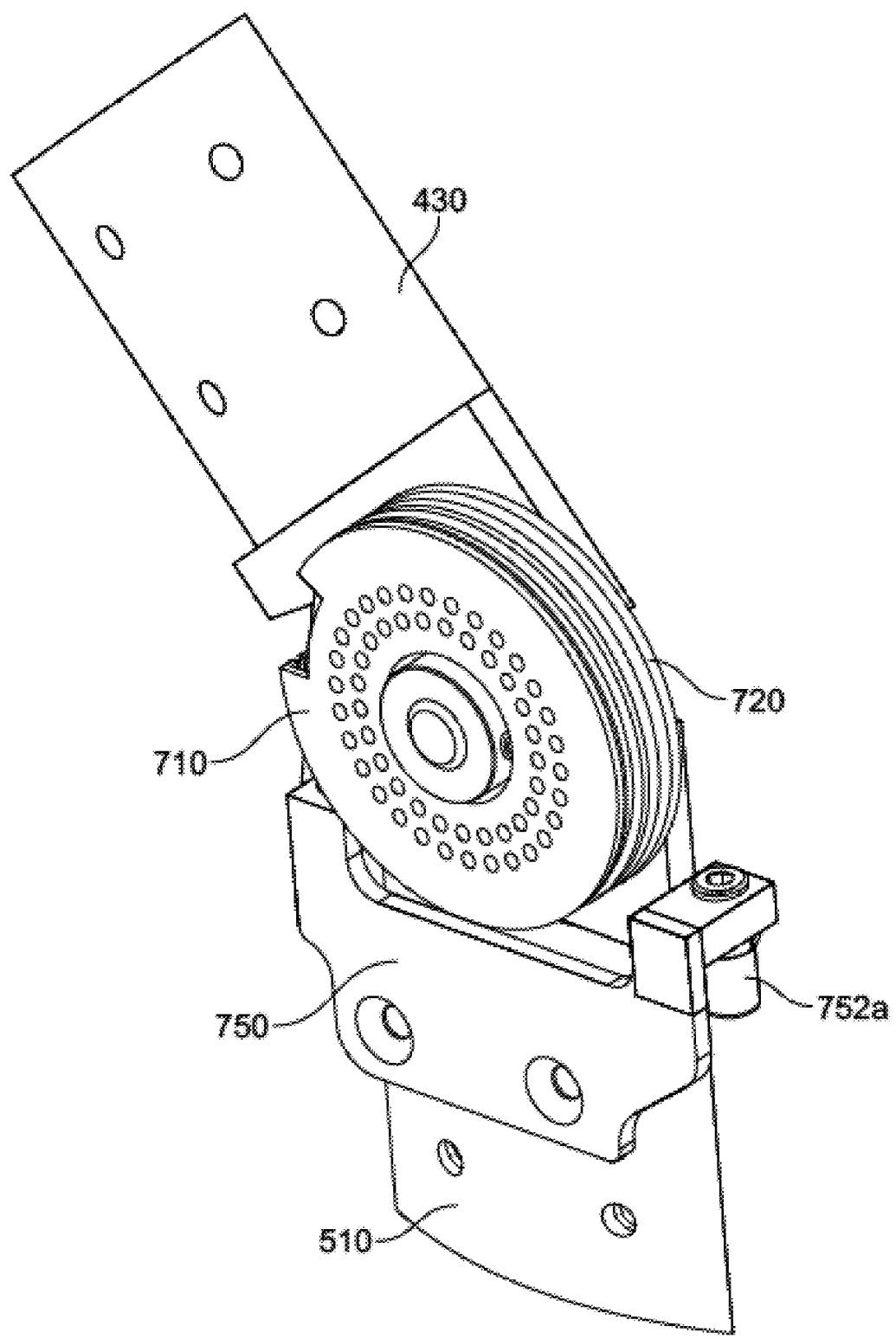
FIG. 10C is an isolated perspective view of a terminator plate coupled to the knee joint.
Figure 10D:
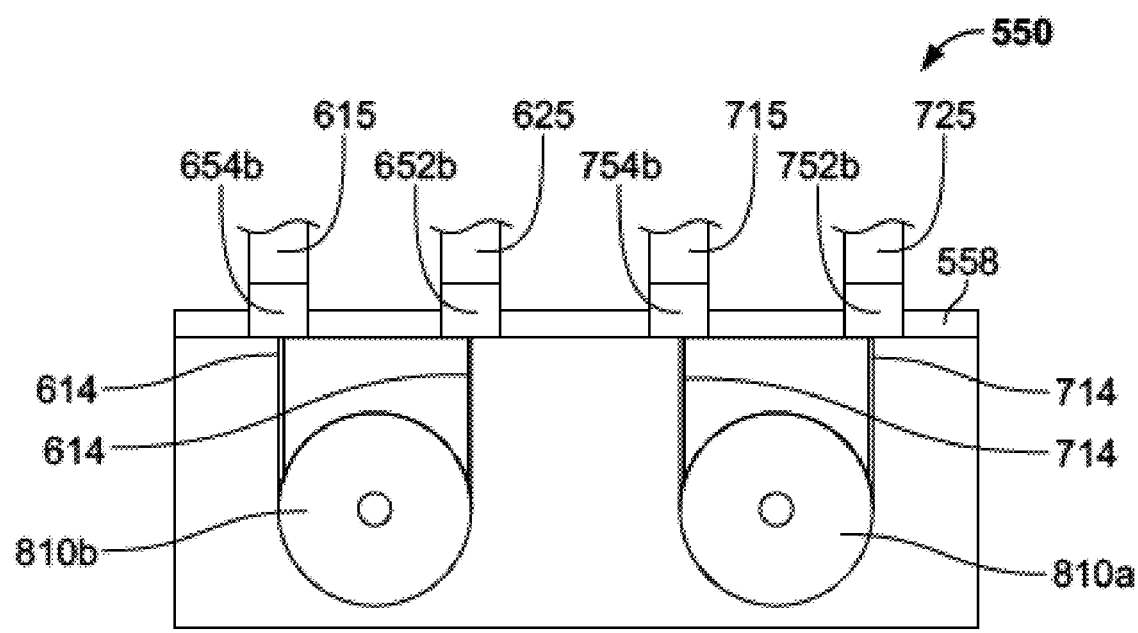
FIG. 10D is a rear cutaway view of the foot module of the exoskeleton showing cables routed to actuators.

Both hip actuators 600 and knee actuators 700 may be driven by similar or identical mechanisms, so only a single drive mechanism for one knee actuator 700 is described, with the understanding that the description may generally apply to the other knee actuator 700 and both hip actuators 600. However, as noted above, it should be understood that the position of the flexion spindle and extension spindle may be opposite between knee actuator 700 and hip actuator 600. Referring to FIGS. 10A-C, flexion spindle 710 includes a channel extending along the circumference of the spindle, an end of the channel terminating in a cutout 712. A wire or cable 714 is routed through flexion spindle 710 along the channel formed therein. An end of the cable 714 may be coupled to a cable swage 716, the cable swage 716 being positioned within the cutout 712 of the extension spindle 710 and effectively rotationally fixing the position of the end of the cable 712 with the cutout 712. Cable swage 716 may take the form of any suitable swage, pressure plate, or any other suitable configuration. As cable 714 is tensioned in a direction away from cable swage 716, the flexion spindle 710 begins to rotate if the maximum flexion position has not been reached. Cable 714 may extend away from cable swage 716, be routed to another spindle connected to an actuator within foot module 550 (this is described in greater detail below), and then routed back up through a channel formed in extension spindle 720. The end of the portion of cable 714 wrapped around extension spindle 720 may also end in a cable swage 726 positioned within a cutout of extension spindle 720. When tension is placed on cable 714 in the direction opposite second cable swage 726, the extension spindle 720 begins to rotate if the maximum extension position has not been reached and has not been otherwise limited by software based upon information determined from sensors. With this configuration, a single cable 714 has a first end rotationally fixed to flexion spindle 710 via cable swage 716 and a second end rotationally fixed to extension spindle 720 via cable swage 726, with a middle portion of the cable wrapped around a spindle coupled to an actuator within the foot module 550. Thus, actuation of the spindle in the foot module 550 in a first rotational direction causes knee actuator 700 to rotate to cause flexion, while rotation of the spindle in the foot module 550 in the opposite direction causes knee actuator 700 to rotate to cause extension. Cable 714 may be formed from metals including steel, composites, natural sinews, inorganic sinews, or combinations thereof.

The cable routing is shown in greater detail in FIGS. 10B-E. Referring to the knee actuator 700 shown in FIG. 10B, one end of cable 714 terminates in cable swage 716 on flexion spindle 710, while the other end of cable 714 terminates in cable swage 726 on extension spindle 720. The cable 714 is routed to an actuator spindle 810a positioned within foot module 550, the spindle 810a being coupled to an actuator 800a that may rotate the spindle 810a, such as a motor. When the actuator 800a causes the spindle 810a to rotate in a first direction, tension is placed on cable swage 716 via cable 714, causing knee actuator 700 to flex the knee joint, while rotation of the spindle 810a in the opposite direction puts tension on cable swage 726 via cable 714, causing knee actuator 700 to extend the knee joint. The particular configuration of cable 714 in relation to spindle 810a is described in greater detail below. It should be understood that, although a single cable 714 is shown wrapped around spindle 810a, two separate cables may be used. For example, one cable may be coupled at a first end to flexion spindle 710, for example via a cable swage, with the second end coupled to spindle 810a, for example via another cable swage. Similarly, a second cable may be coupled at a first end to extension spindle 710, for example via cable swage, with the second end coupled to spindle 810a, for example via another cable swage.

In order to reduce friction caused by movement of exposed cables, such as cable 714, and to increase the flexibility and ability to route moving cables as desired, Bowden cables with corresponding terminators may be used. For example, as shown in FIG. 10B, cable 714 is routed from cable swage 716, around flexion spindle 710, and through Bowden cable 715, or any other suitable tube-like conduit. Similarly, the other end of cable 714 is routed from cable swage 726, around extension spindle 720, and through Bowden cable 725. Bowden cables act as low friction conduits so that other cables or wires, such as cable 714, may move without exposing the moving cable 714 to undesired objects, such as components of exoskeleton 100 or the user, which may cause undesired friction and/or harm to the user. The Bowden cables also provide ability to route the moving inner cable 714 in any desired manner, eliminating the need for line-of-sight routing needed in pulley systems, for example. Each Bowden cable may be coupled to exoskeleton 100 at each end of each Bowden cable via a terminator. For example, as shown in FIG. 10C, a terminator plate 750 may be coupled to lower knee bracket 510, for example by passing fasteners through corresponding apertures in terminator plate 750 and lower knee bracket 510. A first end of terminator plate 750 may include a coupling 752a, with the opposite end of terminator plate 750 including another coupling 754a (FIG. 10B). Although the couplings described herein may be described as being part of a terminator plate, they may alternately be provided separate from the terminator plates. For example, coupling 752a may be provided as part of lower knee bracket 510. The top end of each coupling 752a, 754a may be open to allow for cable 714 to enter/exit the coupling, with Bowden cable 715 being coupled to the bottom of coupling 754a and Bowden cable 725 coupled to the bottom of coupling 752a. These terminators receive the wire routing tubing such as Bowden cable 715 in a fashion that the wire 714 exits the routed housing linear with that of the rotational plane of the respective spindle. It should be understood that the various Bowden cables described herein could be routed as desired, for example inside the various panels described herein or along the outside of the panels, such as along the edges of the panels.

The description provided above with respect to cable 714 of knee actuator 700 generally applies to hip actuator 600. For example, referring to FIG. 10B, hip actuator 600 may include a cable 614 with a first end attached to cable swage 616 and a second end attached to cable swage 626. Cable 614 may be routed from cable swage 616, around extension spindle 610, and through Bowden cable 615 via terminator coupling 654a. Similarly, the other end of cable 614 may be routed from cable swage 626, around flexion spindle 620, and through Bowden cable 625 via terminator coupling 652a.

Each Bowden cable 615, 625, 715, and 725 may extend from an associated terminator coupling at the hip/knee joint to another coupling on foot module 550. It should be understood that a terminator plate similar or identical to terminator plate 750 may be provided at the hip joint to facilitate coupling to Bowden cables 615, 625. As shown in the cutaway rear view of foot module 550 in FIG. 10D, terminator couplings 652b, 654b, 752b, 754b may be coupled to a top surface of foot module 550. Terminator couplings 654b, 652b, 754b, and 752b may couple to an end of Bowden cables 615, 625, 715, and 725, respectively. Cable 615 extends through coupling 654b, wraps around spindle 810b, and passes back through coupling 652b. Alternatively, as described above, the cable 615 may take the form of two separate cables, each having an end coupled to spindle 810b, for example via cable swages. Similarly, cable 714 extends through coupling 754b, wraps around spindle 810a, and passes back through coupling 752b. Terminator couplings 652b, 654b, 752b, and 754b may also function as tensioners, increasing or decreasing the amount of tension on the Bowden cable associated with the particular terminator coupling. This tensioning may help reduce the amount of play in the cable system. Such tensioning may be provided, for example, via a threaded connection between a particular Bowden cable and an associated terminator coupling.

Figure 10E:
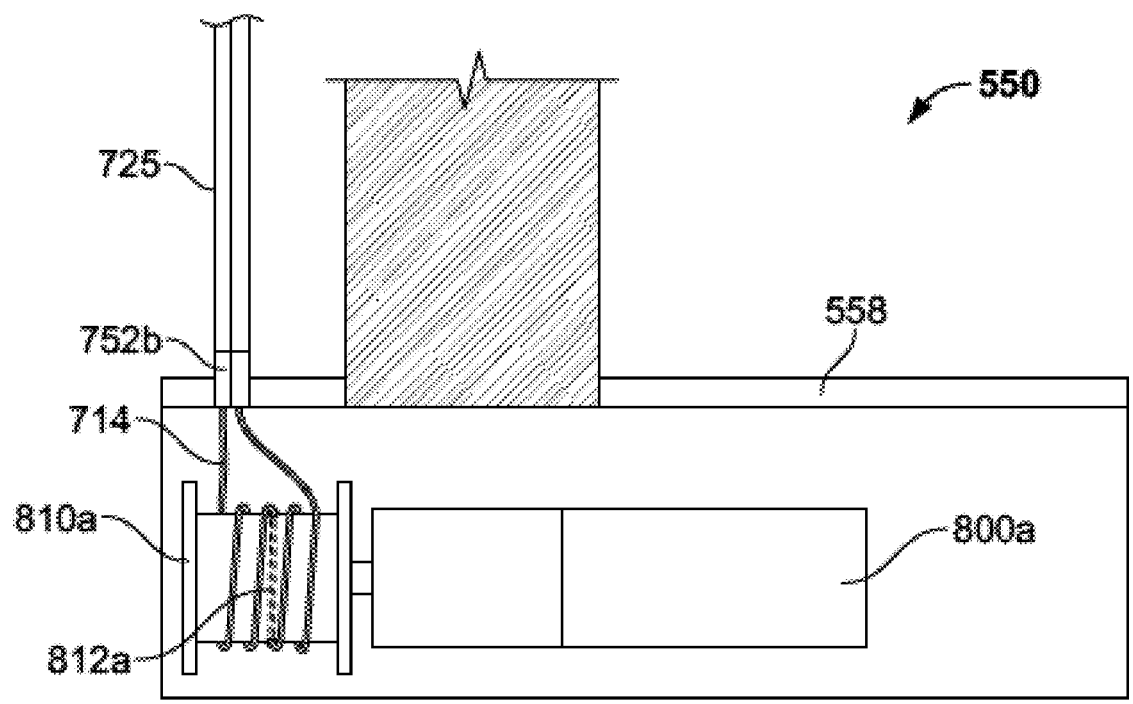
FIG. 10E is a side cutaway view of the foot module of the exoskeleton showing cables routed to actuators.

FIG. 10E shows a detailed view of cable 714 wrapped around spindle 810a. Actuator 800b and spindle 810b are omitted from this view, but it should be understood that actuator 800b and spindle 810b may be positioned within foot module 550 adjacent actuator 800a and spindle 810a. As shown, cable 714 is wrapped two times around spindle 810a, fed through a channel 812a (represented in the figure as a hashed line) passing through a diameter of the spindle 810a, wrapped two more times around spindle 810a, and routed back up through terminator coupling 754b (not visible in FIG. 10E). It should be understood that different number of wrappings and a different diameter spindle may be used to achieve a desired pulley ratio. With this configuration, actuator 800a may have the ability to rotate spindle 810a in a first direction to cause extension of knee joint 700, and the ability to rotate spindle 810a in a second direction opposite the first direction to cause flexion of knee joint 700. Further, because a single cable 714 is transmitting power from actuator 800a, knee joint 700 remains tensioned throughout the entire range of flexion and extension, without an opportunity for slack to develop. In particular, during assembly, extension spindle 720 may be fastened to upper knee bracket 430 as described above, with cable 714 routed down to spindle 810a and back up to flexion spindle 710. Before fastening flexion spindle 710 to extension spindle 720, flexion spindle 710 may be rotated with respect to extension spindle 720 to create a desired amount of tension in cable 714. Once the desired tension is reached, which may be enough tension to eliminate any "play" in the system, extension spindle 720 may be fastened to flexion spindle 710, with the desired tension remaining substantially constant through extension and flexion of knee joint 700. The torque on flexion spindle 710 may be applied prior to attachment to extension spindle 720, for example, with a spreader wrench, automatic tensioning device such as an independent actuator, winch-type tensioner, or the like. Actuator 800b and spindle 810b may be configured in the same manner relative to cable 614 and hip joint 600 as described with respect to actuator 800a, spindle 810a, cable 714, and knee joint 700. Actuator spindles 810a and 810b may be formed of metals, such as aluminum, steel, titanium, brass, or alloys thereof, plastics, composites, inorganics, organics, or combinations thereof. As described above, cable 614 and/or cable 714 may each take the form of two distinct cables coupled to a joint spindle at a first end and a motor spindle at the second end, for example via cable swages, to provide similar or identical functionality to the single cable embodiment.

Actuators 800a and 800b may be, for example, electric motors such as AC or DC motors, both brushed and brushless, electronically commutated motors (ECM's), stepping motors, hydraulic actuators, pneumatic actuators and combinations thereof. As shown, actuators 800a and 800b may be grouped together, for example two actuators per foot module, which may allow all or substantially all of the energy and electrical components to be provided as single units (or multiple segmented units). In addition, it should be understood that actuators 800a and 800b are capable of being positioned in locations relatively far away from the rotational axes of their corresponding joints (e.g. the center of knee joint 700 is the rotational axis controlled by actuator 800a and the center of hip joint 600 is the rotational axis controlled by actuator 800b). This configuration allows the actuators 800a and 800b to be substantially position-independent of the relatively bulky knee actuator 700 and hip actuator 600, which in turn allows exoskeleton 100 to have reduced areas of bulk compared to exoskeletons using traditional actuators. For example, in the illustrated embodiment, actuators 800a and 800b are positioned within foot module 550, which allows for a reduction of bulk at or near hip actuator 600 and knee actuator 700.

The control of the hip actuators 600 and knee actuators 700 may take different forms. For example, one or more main processors may be positioned in any suitable location in exoskeleton 100, but preferably within foot module(s) 550 adjacent actuators 800a and 800b which physically drive the joints. The main processor units may include microcontrollers, processors, PCBs and the like. The main processor unit(s) may perform most or all of the computations which guide the movements of exoskeleton 100, deciphering the feedback provided by the one or more sensors described in greater detail below. Depending on the information processed by the main processor unit(s), certain actuators 800a, 800b will be targeted to perform different tasks in order to perform a movement.

The general control architecture may be thought of as being separate into three levels of hierarchy, including basic control, intermediate control, and advanced control.

At a basic control level, movement of hip actuators 600 and knee actuators 700 may be controlled by a stride switch and/or a weight sensor. A stride switch may be located on any conveniently accessible portion of exoskeleton 100, although more preferably the stride switch is located on an external component used in combination with exoskeleton 100. For example, a joystick or other hand-held controller may extend from upper extremity section 200 (not illustrated), or the stride switch may be located on a secondary mobility aid, such as a walker, cane, or crutches, with the stride switch being operatively coupled to the main processor unit(s). The stride switch may, for example, include a first button to initiate a stride of the right leg support, driven by the hip and knee actuators 600 and 700 on the right leg, and a second button to initiate a stride of the left leg support, driven by the hip and knee actuators 600 and 700 on the left leg. Other inputs may be possible, such as a button corresponding to a stand function and another button corresponding to a sit function. Weight sensors may also be included in exoskeleton 100, for example in the sole 558 of each foot module 550. The weight sensors may determine how the user's weight is positioned on each foot module 550. When used in combination with the stride sensor, the weight sensors may not allow a user to initiate a stride if his or her weight is not positioned correctly. For example, if the user is generally putting most or all of his or her weight on his or her heels, as determined by the weight sensors, the main processor unit(s) may prevent the user from initiating a stride with the stride switch. If the user's weight is balanced correctly, the main processor unit(s) may determine that the desired stride may be initiated upon activation of the stride switch. Alternately, the weight sensors may provide enough information to the main processor unit(s) to allow them to determine that a user is attempting to begin a stride, and the main processor unit(s) may then activate the hip and knee joints as necessary to facilitate the user in completing the stride. The system dynamics provided with the basic controls may be best suited for inexperienced users or users with relatively simple mobility needs, but may be useful in a variety of situations, including, for example, a rehabilitation setting, depending on a particular user's needs.

As an intermediate control level, a number of additional sensors may be utilized together or separately to further facilitate a user of the exoskeleton 100 in performing or completing a particular movement. In other words, the intermediate level controls provide for more fine-tuned driving of hip actuator 600 and knee actuator 700 by their associated actuators 800b and 800a. For example, inertial measurement units ("IMUs") may be positioned at different locations on exoskeleton 100, including within the sole 558 of one or both foot modules 550. For example, IMUs may be located on one or both foot modules 550, below and above one or both hip actuators 600, and below and above one or both knee actuators 700. This configuration may provide for triangulation of the position of each joint. IMUs may use a combination of measurement devices, for examples accelerometers, magnetometers, and gyroscopes, to determine orientation, position, speed, acceleration, rotational speed, and/or forces experienced by the device to which the IMUs are attached. For example, IMUs may be used to triangulate or otherwise map the position of the vertices of the hip joints 600 and knee joints 700. With the information provided by the IMUs, the main processing unit(s) may be able to determine where components of exoskeleton 100 are in space relative to one another, as well as what type of movement and/or forces are being experienced by components of exoskeleton 100, helping refine signals being sent to the actuators 800a and 800b to drive movement of the exoskeleton 100. In this intermediate control mode, users may be able to traverse a multitude of steep and off-kilter environments because of increased feedback awareness.

Other sensors may be used with exoskeleton 100 in addition or as an alternative to IMUs, including, for example, rotary position sensors that measure rotational speed, direction, and/or position. The rotary position sensor, or other rotary measurement device, may be used to determine the rotational position of each joint relative to one another, and thus determine the position of each component of the exoskeleton 100. The system dynamics provided with the intermediate controls may be best suited for users that desire or need to traverse a multitude of steep and/or off-kilter environments, which is made possible by exoskeleton 100 at least in part due to increased feedback awareness.

More advanced sensors may provide an advanced control level to even further facilitate a user of the exoskeleton 100 in performing or completing a particular movement. In other words, the advanced level controls provide for even finer tuned driving of hip actuator 600 and knee actuator 700 by the associated actuators 800b and 800a. For example, a number of muscle sensors that detect, for example, electromyogram ("EMG") signals may operatively connect the main processing unit(s) to the muscles of the user in exoskeleton 100. If a user attempts to initiate a movement, for example by flexing leg muscles in an attempt to lift a foot to initiate a step, the muscle sensors may detect this signal, with the main processing unit(s) interpreting the signal and causing actuators to drive movement of the hip actuator 600 and knee actuator 700 as necessary to complete the movement. Muscle sensors may be placed nearly anywhere on the body, such that even a disabled user may control exoskeleton 100 via muscle signals. In addition or as an alternative to muscle signal sensors, exoskeleton 100 may include EEG sensors operably coupled to the main processing unit(s). EEG sensors detect brain activity, as represented by varying Hertz frequencies. The detected Hertz frequencies may be compared to pre-programmed functions of Hertz frequencies that correspond to particular desired movements. When brain activity is detected that matches a pre-programmed function, the main processing unit(s) may instruct the actuators 800a and 800b to perform a movement corresponding to the pre-programmed function. The system dynamics provided with the advanced controls may not increase performance capabilities of exoskeleton 100 in particular environments compared to the intermediate level of control described above, but the advanced levels of control provide a user with substantially complete control of the movement of exoskeleton 100.

Exoskeleton 100 may also include a number of gyroscopes to facilitate desired movement or to inhibit undesired movement. For example, gyroscopes may be positioned at any desired locations on exoskeleton 100 to help prevent a user from falling. If, through any of the various sensors described herein, the processor determines that a user is beginning to fall in any direction, the gyroscopes may activate to inhibit that undesired movement and to maintain a desired orientation. With the ability to determine the location of the components of exoskeleton 100 with respect to one another, the gyroscopes may also assist a user in making specific movements which correspond to the user's environment. For example, if a user is traversing up a set of stairs, the gyroscopes may impede the user from falling backwards and could, in some instances, also prevent the user's legs from impacting objects such as stair risers. In the aforesaid example, gyroscopes may be located on the lower extremities of exoskeleton 100 and/or on the torso support.

Other sensors that may be provided with exoskeleton 100 include environmental detection sensors. For example, infrared sensors, proximity sensors, ultrasonic sensors, pressure sensors, or other suitable sensors may be positioned at various locations on exoskeleton 100 to determine objects proximate to exoskeleton 100. With such environmental detection sensors, exoskeleton 100 may not only detect the positions of components of exoskeleton 100 in relation to one another, but also in relation to the user's environment. In the example above regarding gyroscopes inhibiting a user's leg from hitting a stair riser while traversing a set of stairs, the environmental detection sensors may provide the information to the main processor unit(s) to determine the location of the stair riser, which may be used to activate the gyroscopes and/or limit actuators, if necessary, to inhibit the lower leg of the exoskeleton 100 from striking the stair riser.

Software in communication with the main processing unit(s) may help convert information provided by sensors or otherwise input to the main processing unit(s) into control signals for the actuators 800a and 800b. For example, PID controls may include algorithms to calculate current values, average values, and expected values, and based on that data set, adjust the output of the actuators 800a and 800b based upon the input of the PID algorithm. As an example, exoskeleton 100 may provide the necessary force to move a 200 pound adult or a young child in a substantially identical fashion without user-specific changes to the software being required. Other software may include IMU tracking software if IMUs are utilized. IMU tracking software may determine the location of each IMU unit and determine at what moment to engage the actuators 800a and 800b of exoskeleton 100 to create desired motion. In one example, each IMU must meet certain threshold values, such as a particular angle or spatial position, in order to allow actuators 800a and 800b to be triggered. The IMU tracking software may be used in conjunction with information determined from the environmental sensors to facilitate motion of components of exoskeleton 100 both with respect to one another and with respect to the user's environment.

One or more power supplies may be included with exoskeleton 100 to provide power to the mechanical and electronic systems described above. For example one or more batteries may be positioned on or within exoskeleton 100. Preferably, the one or more batteries are positioned within the compartment of foot module 550 defined by upper foot platform 554 and lower foot platform 552. In this configuration, the one or more batteries may be adjacent actuators 800a and 800b, as well as other electronic components such as the main processing unit(s). Among other benefits, this configuration allows the one or more batteries, which may be relatively bulky, to be placed out of sight with the other components within foot modules 550. However, if additional power supplies are desired, low profile cells may be embedded under padding located along the upper leg panel 420 and/or lower leg panel 520 and or torso support 210.

Although a number of features of exoskeleton 100 are described above in connection with the figures, it should be understood that a number of variations or alternatives may be provided without departing from the spirit of the invention. For example, foot modules 550 are described above as including a static connection between the foot modules 550 and lower leg panels 520. An articulation mechanism may be included at the connection point(s) between foot modules 550 and lower leg panels 520 to provide for the ability for a user to articulate his or her ankle(s) while using exoskeleton 100. This may facilitate mobility in relatively harsh terrain, for example. In addition, with the use of connections that provide an articulating ankle joint, the forward angle of sole 558 of foot module 550 may be eliminated.

Figure 11:
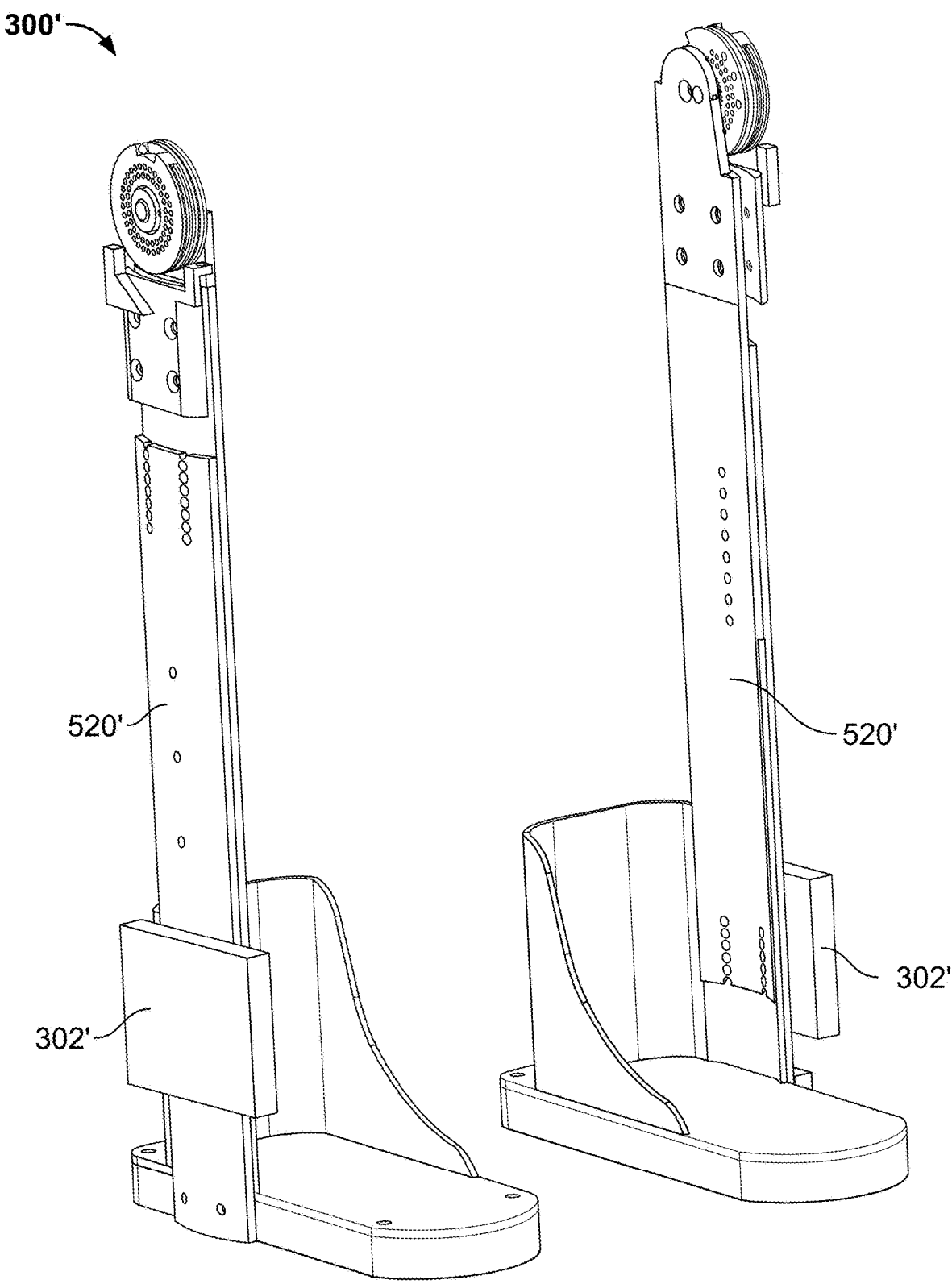
FIG. 11 is an isolated perspective view of a lower leg section of an exoskeleton according to another embodiment of the invention.

Still other alternatives may be provided. For example, as described above, the actuator and cable routing systems described herein provide the ability for actuators 800a and 800b to be located away from the rotation axes of the hip actuator 600 and knee actuator 700. Although in one embodiment the actuators 800a and 800b may be placed in the foot modules 550 to reduce bulk of exoskeleton 100 such that it may be worn inconspicuously under the clothing of a user, other positioning is possible. For example, as shown in FIG. 11, in an alternate embodiment, an exoskeleton may include an alternate lower leg section 300' that is mostly identical to lower leg section 300, with a few variations. For example, Rather than a foot module 550 that includes a compartment for the actuators 800a, 800b, spindles 810a, 810b, and associated electronics, lower leg section 300' moves those components to separate low profile compartments 302' attached to lower leg panels 520'. This compartment 302' may contain the actuators and spindles described as being positioned in the compartment of foot module 550 of exoskeleton 100. For example, Bowden cables (not pictured) may extend from the hip and knee joints into couplings on compartment 302', with moving cables extending through those Bowden cables and connected to associated spindles and actuators within compartment 302'. At least because the systems described herein allow positioning of actuators of the knee and hip joints away from the rotational axes of the knee and hip joints, such a compartment may be provided nearly anywhere in relation to the exoskeleton. This freedom in positioning provides, at least in part, the ability for the exoskeletons described herein to retain a low profile, which may facilitate the use of the exoskeleton in a relatively inconspicuous manner, for example by wearing the exoskeleton substantially under a user's clothing. For example, a compartment similar to compartment 302' may be positioned alternatively on the upper leg panels, the torso panels, or on or within the torso support, for example, to allow for driving of the hip and knee joints while maintaining a low profile.

Still other components may be added to exoskeleton 100 or variations thereof without departing from the scope of the invention. For example, although omitted from the drawings, covers may be provided at or along any joint of exoskeleton 100 to protect a user from being pinched from joint movement. Other protective covers may be provided at any position on exoskeleton 100 where it is desirable to cover or otherwise conceal a structure of exoskeleton 100.

Although generally described above for use by users with some form of leg weakness or disability, it should be understood that exoskeleton 100 and variations thereof have a number of real world applications. For example, exoskeleton 100 may function as an assistive suit to facilitate rehabilitation or to facilitate typically strenuous or repetitive work, such as assembly line or other manufacturing work. Other assistive uses may include military use to enhance the user's mobility, or for use in training and/or simulations. For example, exoskeleton 100 or variations thereof may be used for testing garments such as Hazmat suits, or to train able-bodied individuals to walk again, for example a patient who has lost the full ability to walk after experiencing a coma. Exoskeleton 100 or variations thereof may also be used to replicate a complex movement or series of movements, such as a dance, to facilitate a user in learning the movement(s). In other applications, exoskeleton 100 may function as an enabling suit. This may include, for example, users who have some form of weakness or disability, such as users with paralysis, including paraplegics and quadriplegics, amputees, elderly users, obese users, users bound to a wheel chair, or otherwise physically disabled users. Exoskeleton 100 may also include telerobotic applications. For example, a doctor may control an exoskeleton 100 coupled to a patient remotely, to help determine where in a gait a user may feel pain. In other telerobotic applications, a user may remotely control, for example, a soldier or other person who has lost the ability to control exoskeleton 100. Even further, telerobotic applications may include the control of exoskeleton 100 without any user coupled to the suit, in effect turning exoskeleton 100 into a humanoid robot to perform any number of desired tasks.

Figure 12:
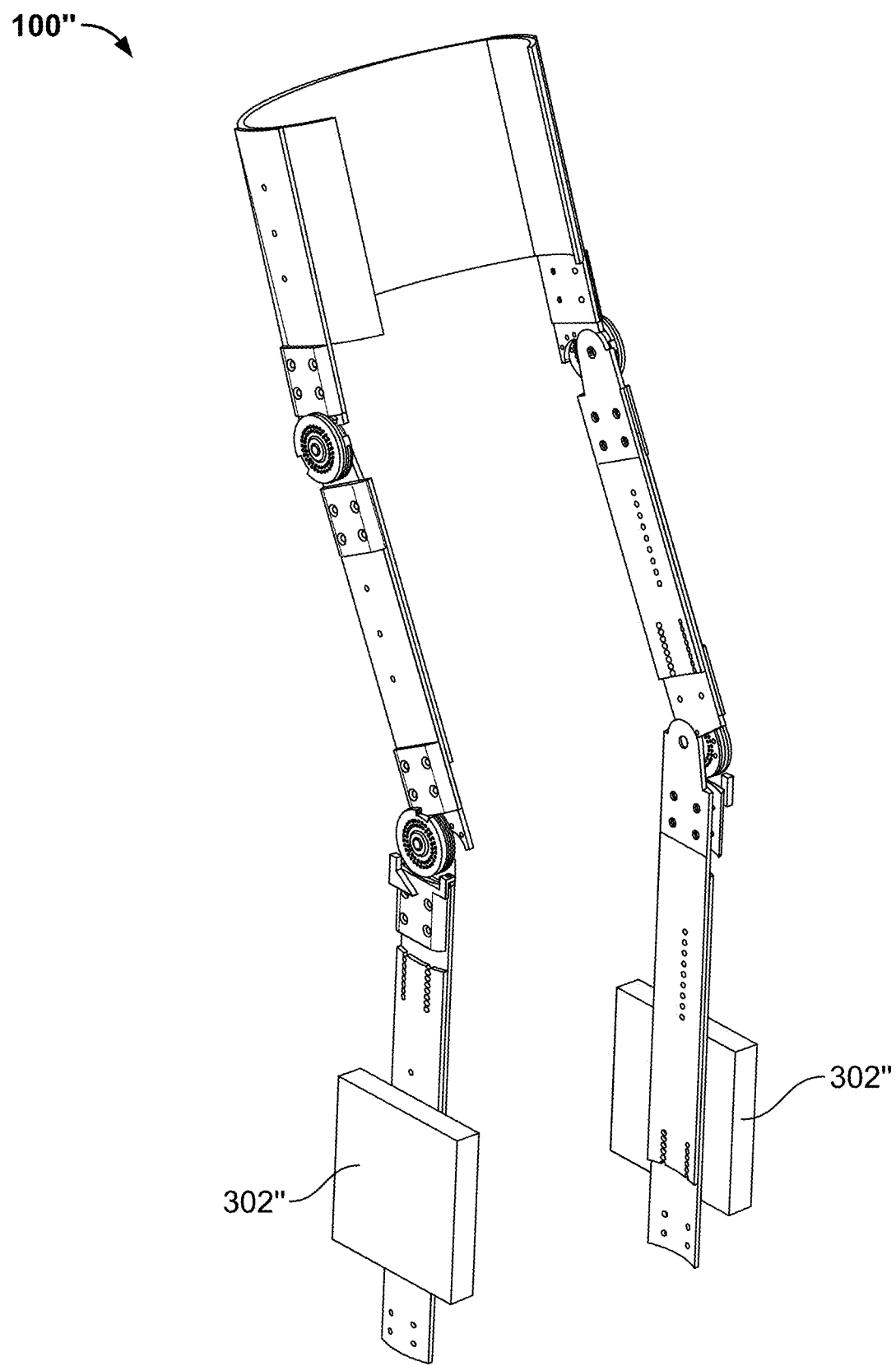
FIG. 12 is a perspective view of an exoskeleton according to a further embodiment of the invention.

In an embodiment in which the exoskeleton is designed for an able bodied user, the entire foot module 550 described in connection with exoskeleton 100 may be removed, allowing the user's foot to directly contact the ground (with or without use of shoes or other footwear). In that embodiment, shown in FIG. 12, the exoskeleton 100" may include the actuators and other controls in a compartment 302" similar to that shown in FIG. 11 or the alternatives described in connection with FIG. 11.

The features and configurations of exoskeleton 100 (and variations thereof) described herein provides significant adjustability so that a single size or configuration may be adjusted to fit all or substantially all potential users, regardless of weight, height, and body shape. Further, with the above described configurations, exoskeleton 100 and variations thereof may be coupled to a user with most or all components extending less than about 1 inch to about 2 inches from the user's body. However, it should be noted that foot module 550 of exoskeleton 100 may extend greater than about 1.5 inches below the user's foot. Because of the location of foot module 550 below the user's foot, exoskeleton 100 may still be substantially inconspicuous when worn.

Figure 13A:
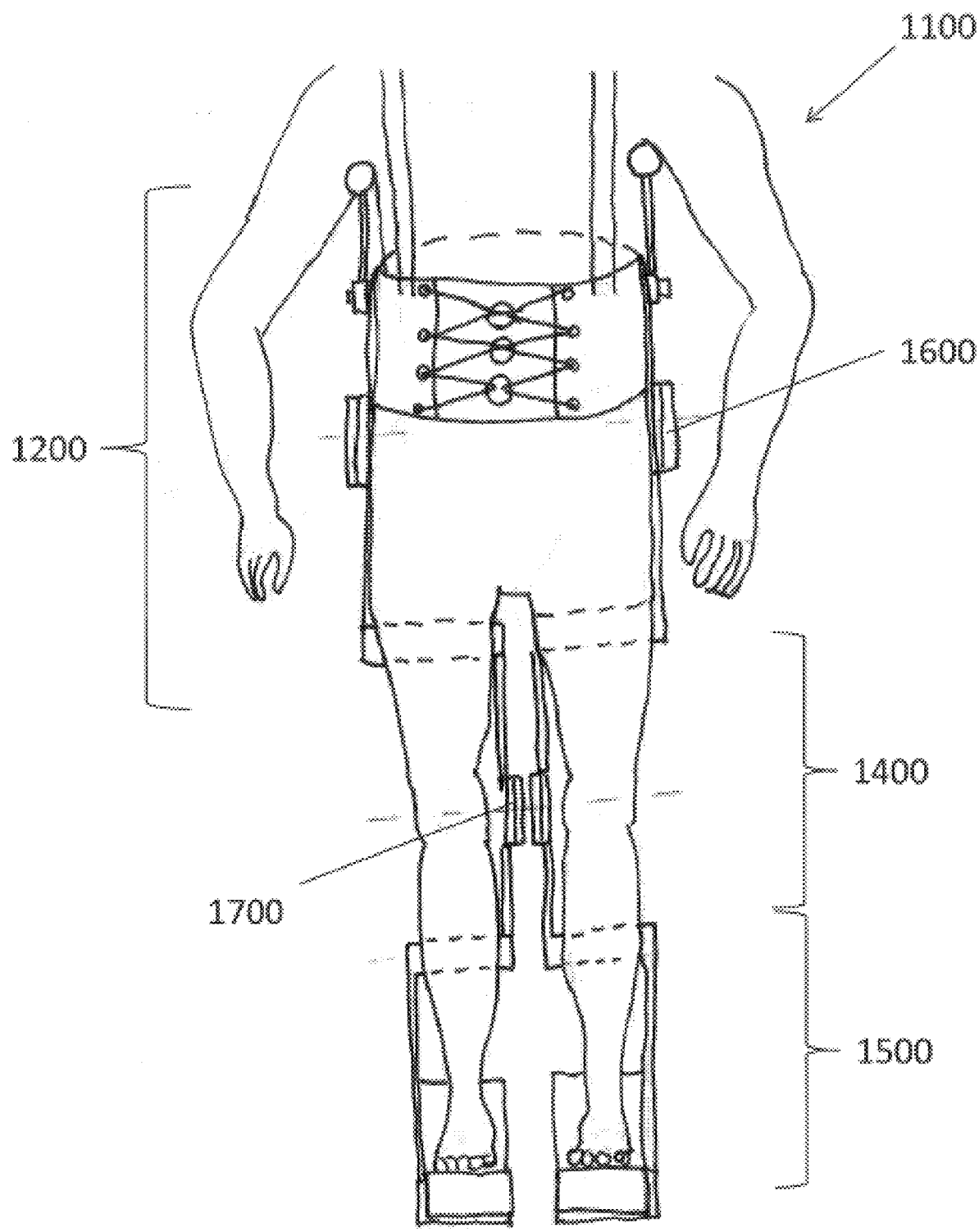
FIGS. 13A-C illustrate an exoskeleton according to another embodiment of the disclosure.
Figure 13B:
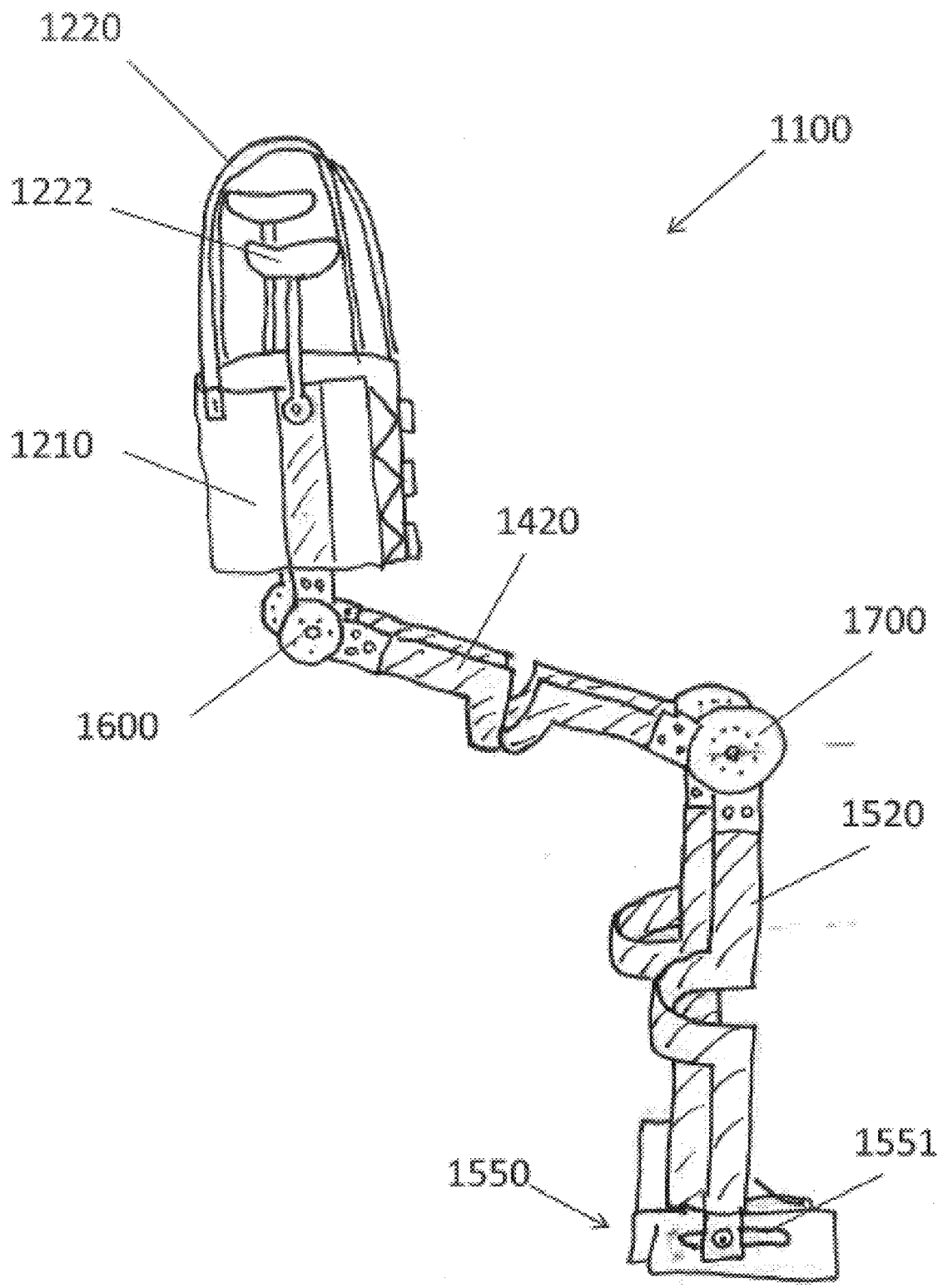

Another embodiment of exoskeleton 1100 is illustrated in FIGS. 13A-B. Similar to exoskeleton 100, exoskeleton 1100 may include an upper extremity portion 1200, an upper leg section 1400, and a lower leg section 1500. Generally, exoskeleton 1100 may function substantially identically to exoskeleton 100. For example, exoskeleton 1100 may include hip actuators 1600 and knee actuators 1700 substantially identical to hip actuators 600 and knee actuators 700 of exoskeleton 100. However, certain differences of exoskeleton 1100 are described below.

As best seen in FIG. 13B, upper extremity portion 1200 may generally include a torso support 1210 and torso straps 1220. Torso support 1210 may further include underarm supports 1222. Underarm supports 1222 may have a first end coupled to torso support 1210, and a second end configured to be positioned in the underarm of the user, as shown in FIG. 13A. The second end of the underarm support 1222 may take a form similar to the top of a crutch and be relatively rigid but comfortable. The underarm supports 1222 function to help lock a user's upper body within exoskeleton 1100. Torso support 1210 may include an upper hip panel coupled to an upper hip bracket, which in turn is coupled to hip actuator 1600, which is coupled to a lower hip bracket. The torso panel, upper and lower hip brackets, and hip actuator 1600 may be substantially identical to those same components described in relation to exoskeleton 100.

Figure 13C:
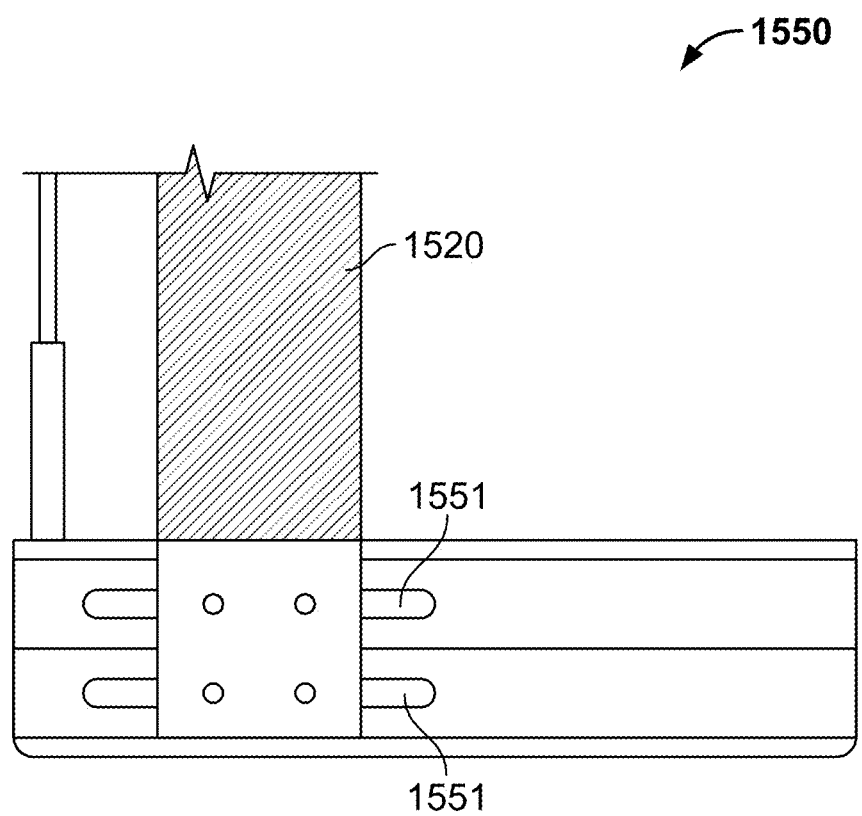

Exoskeleton 1100 may also include upper leg panels 1420 coupling the lower hip brackets to the upper knee brackets. Upper leg panels 1420 may be similar to leg panels 420 described in relation to exoskeleton 100, with at least one exception. Each upper leg panel 1420 may be configured to wrap around a user's upper leg. For example, right leg panel 1420 may be a substantially straight upper portion configured to be positioned along a user's outer thigh, with a middle portion wrapping around the back of the user's thigh, and a substantially straight lower portion configured to be positioned along a user's inner thigh, with the lower portion coupling to the upper knee bracket. The upper knee bracket may connect to knee actuator 1700, which in turn is connected to a lower knee bracket, the lower knee bracket connected to lower leg panel 1520. The configuration of upper leg panel 1420 wrapping around a user's thigh may provide additional support to the user and may facilitate keeping the user more secure within exoskeleton 1100, while maintaining a very low profile. The upper knee bracket, knee actuator 1700, and lower knee bracket may be substantially identical to the corresponding components described in connection with exoskeleton 100. The lower leg panels 1520 may include a wrap-around section similar to upper leg panels 1420. For example, the right lower leg panel 1520 may have a substantially straight upper portion configured to extend along a user's inner lower leg, a middle portion configured to wrap around the back of the user's calf, and a substantially straight lower portion configured to extend along a user's outer ankle. Each leg panel 1520 may be coupled to a foot module 1550, with the foot module 1550 being substantially similar to the foot modules 550 described in connection with exoskeleton 100. One or more slots 1551 are illustrated, as described in relation to exoskeleton 100, to provide for heel-to-toe adjustability of the location at which lower leg panel 1520 couples to foot module 1550. Slots 1551 are illustrated in greater detail in FIG. 13C, with fasteners such as bolts configured to fasten the lower leg panels 1520 to a corresponding foot module 1550 anywhere along the length of slots 1551. Further, with this configuration, knee actuators 1700 may be positioned on the inside of a user's knee, which may further reduce the visible profile of exoskeleton 1100.

It should be noted that in FIG. 13B, knee actuator 1700 is shown as being larger than hip actuator 1600. Although not necessary, providing knee actuators 1700 with larger spindles compared to hip actuator 1600 may assist exoskeleton 1100 in moving the user, for example from a sitting to a standing position. This is in part due to the relatively large force required for such a motion. The mechanical advantage provide by the larger diameter knee actuator 1700 may facilitate such movement. In addition, the wires coupling knee actuator 1700 to motors in the foot module 1550 may also be larger, stronger wires compared to wires associated with hip actuator 1600 to help provide the relatively large force that may be required at knee joint 1700.

Figure 14A:
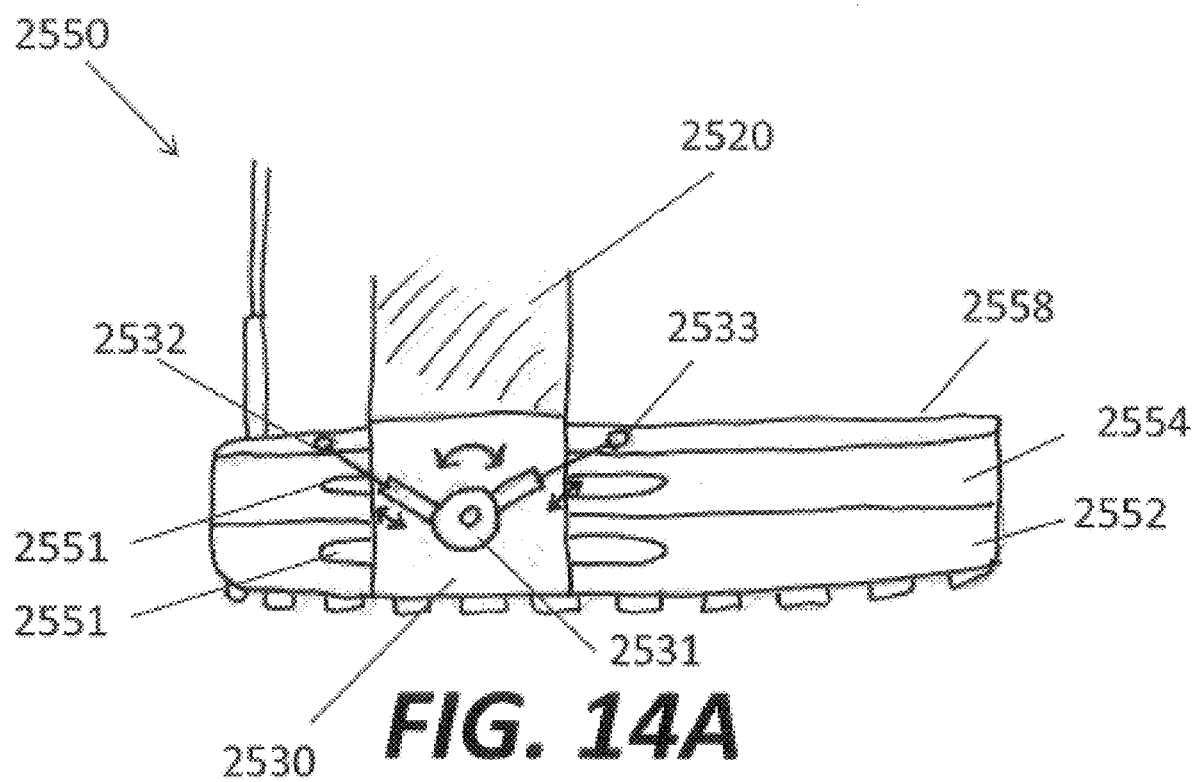
FIGS. 14A-B illustrate a foot module according to a further embodiment of the disclosure.
Figure 14B:
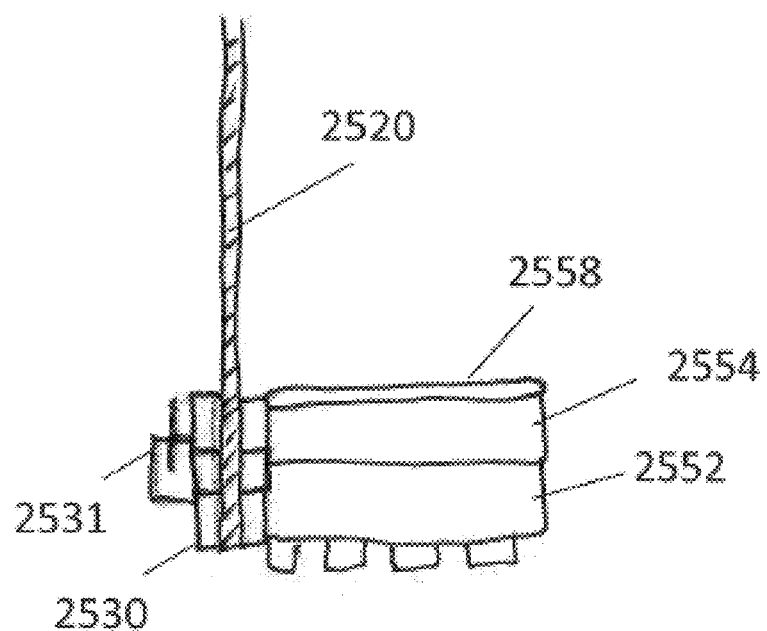

FIGS. 14A-B illustrate side and front views of a foot module 2550 according to another embodiment of the disclosure. Foot module 2550 may be used in place of any other foot module described herein. Similar to foot module 550, foot module 2550 may include a sole 2558 positioned on top of an upper platform 2554, to provide cushioning and/or sensing functionality. A lower platform 2552 may together with upper platform 2554 define an internal compartment in which control mechanisms are positioned. Lower leg panel 2520 may be coupled to foot module 2550 via a foot bracket 2530. As shown best in FIG. 14B, foot bracket 2530 may include two portions sandwiching lower foot panel 2520. A shaft 2531 may extend through foot bracket 2530 and lower leg panel 2520, coupling the foot bracket 2530 and lower leg panel 2520 to foot module 2550 so that foot module 2550 may rotate with respect to foot bracket 2530 and lower leg panel 2520. This configuration provides for articulation at the ankle joint to facilitate movement of the user. Although the shaft 2531 provides for rotation about one axis, a ball joint or other connection may be used to provide additional rotation at the ankle joint.

Still referring to FIGS. 14A-B, a compression and tension system may be included to inhibit free rotation of foot module 2550 with respect to lower leg panel 2520. For example, the compression and tension system may include two members 2532 and 2533. Each member 2532 and 2533 may be coupled to foot module 2550 at a first end, for example at sole 2558, and to the shaft 2531 at the other end. As illustrated, members 2532 and 2533 are linear hydraulic actuators. As a user in the suit moves and rotates his or her ankle, the foot module 2550 rotates along with the user's foot. However, during rotation, one hydraulic linear actuator will slow rotation so that foot module 2550 does not freely rotate about shaft 2531. As foot module 2550 rotates in the other direction, the other hydraulic linear actuator will slow rotation in the other direction.

Figure 15A:
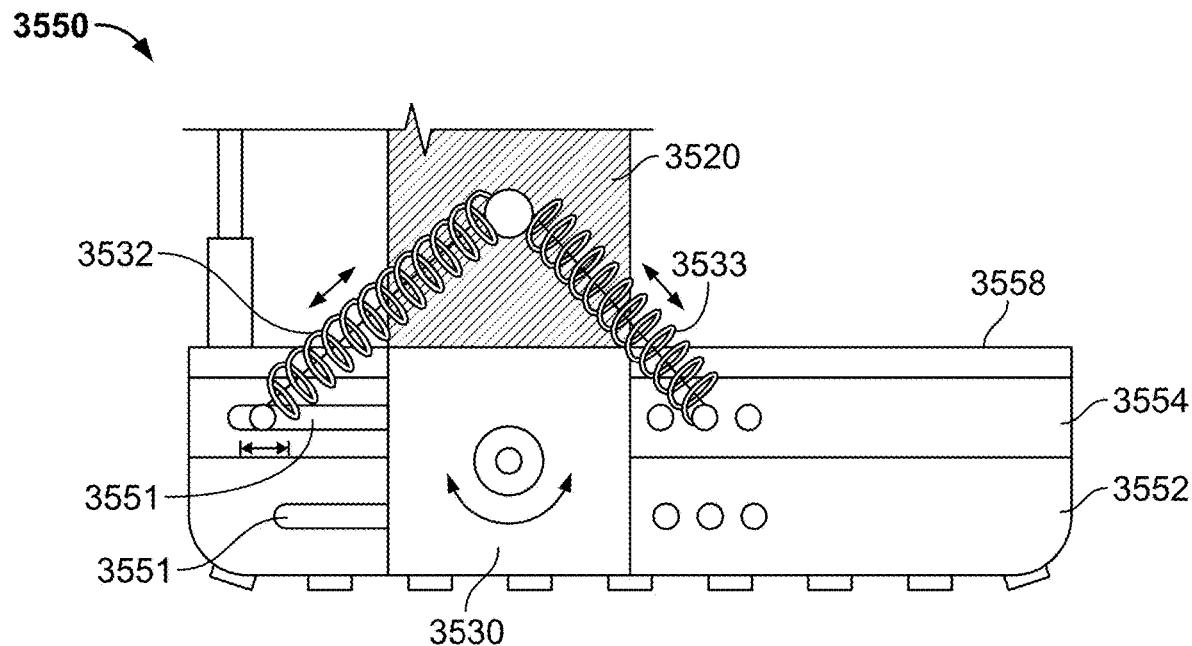
FIGS. 15A-B illustrate a foot module according to yet another embodiment of the disclosure.
Figure 15B:
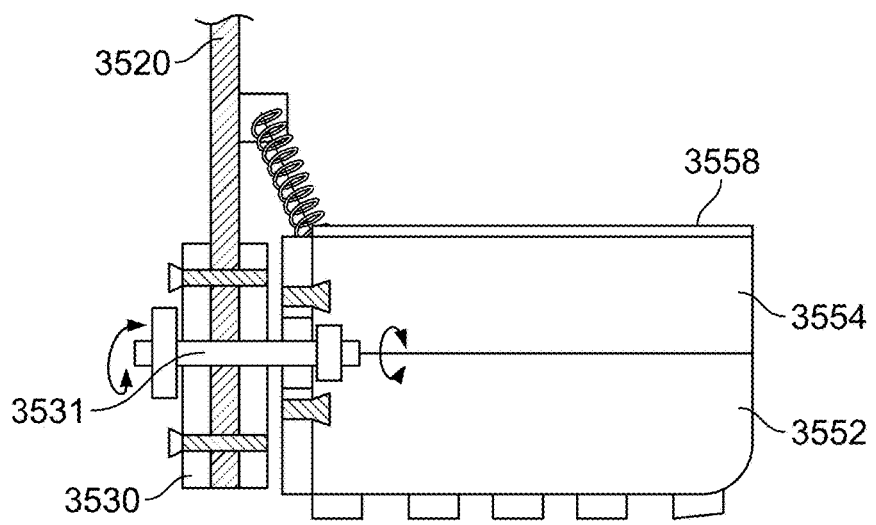

Another embodiment of a foot module 3550 is illustrated in FIGS. 15A-B. As with foot module 2550, foot module 3550 provides for rotation at the ankle and may be used in place of any other foot module described herein. Foot module 3550 may include a sole 3558 positioned on top of an upper platform 3554, to provide cushioning and/or sensing functionality. A lower platform 3552 may together with upper platform 3554 define an internal compartment in which control mechanisms are positioned. Lower leg panel 3520 may be coupled to foot module 3550 via a foot bracket 3530. As shown best in FIG. 15B, foot bracket 3530 may include two portions sandwiching lower foot panel 3520, with the foot panel 3530 coupled to lower leg panel 3520 via fasteners. A shaft 3531 my extend through foot bracket 3530 and lower leg panel 3530, coupling the foot bracket 3530 and lower leg panel 3530 to foot module 3550 so that foot module 3550 may rotate with respect to foot bracket 3530 and lower leg panel 3520.

Still referring to FIGS. 15A-B, a compression and tension system may be included to inhibit free rotation of foot module 3550 with respect to lower leg panel 3520, and to facilitate rotation of the foot module 3550. For example, the compression and tension system may include two members 3532 and 3533. Each member 3532 and 3533 may be coupled to lower leg panel 3520 at a first end. A second end of member 3532 may be coupled to a slot 3551 of foot module 3550. A second end of member 3533 may be coupled to one of a plurality of through holes in foot module 3550. As illustrated, members 3532 and 3533 are springs or spring-like members. As a user in the suit moves and rotates his or her ankle, the foot module 3550 rotates along with the user's foot. However, during rotation, one hydraulic spring will compress and one spring will tension, causing the foot module 3550 to tend to rotate back to an equilibrium position of no rotation. Member 3533 is shown as attached to one of a plurality of through holes in foot module 3550, which may provide for adjustability of tension or compression provided by member 3533. Member 3532 is shown as attached to a slot 3551, which may provide for a floating connection of one end of member 3532. It should be understood that each member 3532 and 3533 may be attached in any desired manner, not just those shown in FIGS. 15A-B. With this configuration, members 3532 and 3533 not only stop free rotation of foot module 3550, but may provide active force. For example, as a user's heel strikes the ground, with the toes pointed upward and the heel pointed downward, member 3533 compresses and member 3532 lengthens. The force created by the springs and/or compression and tension mechanisms 3532 and 3533 tends to rotate foot module 3550 in the other direction, which is the natural movement during the continuation of the step.

Figure 16:
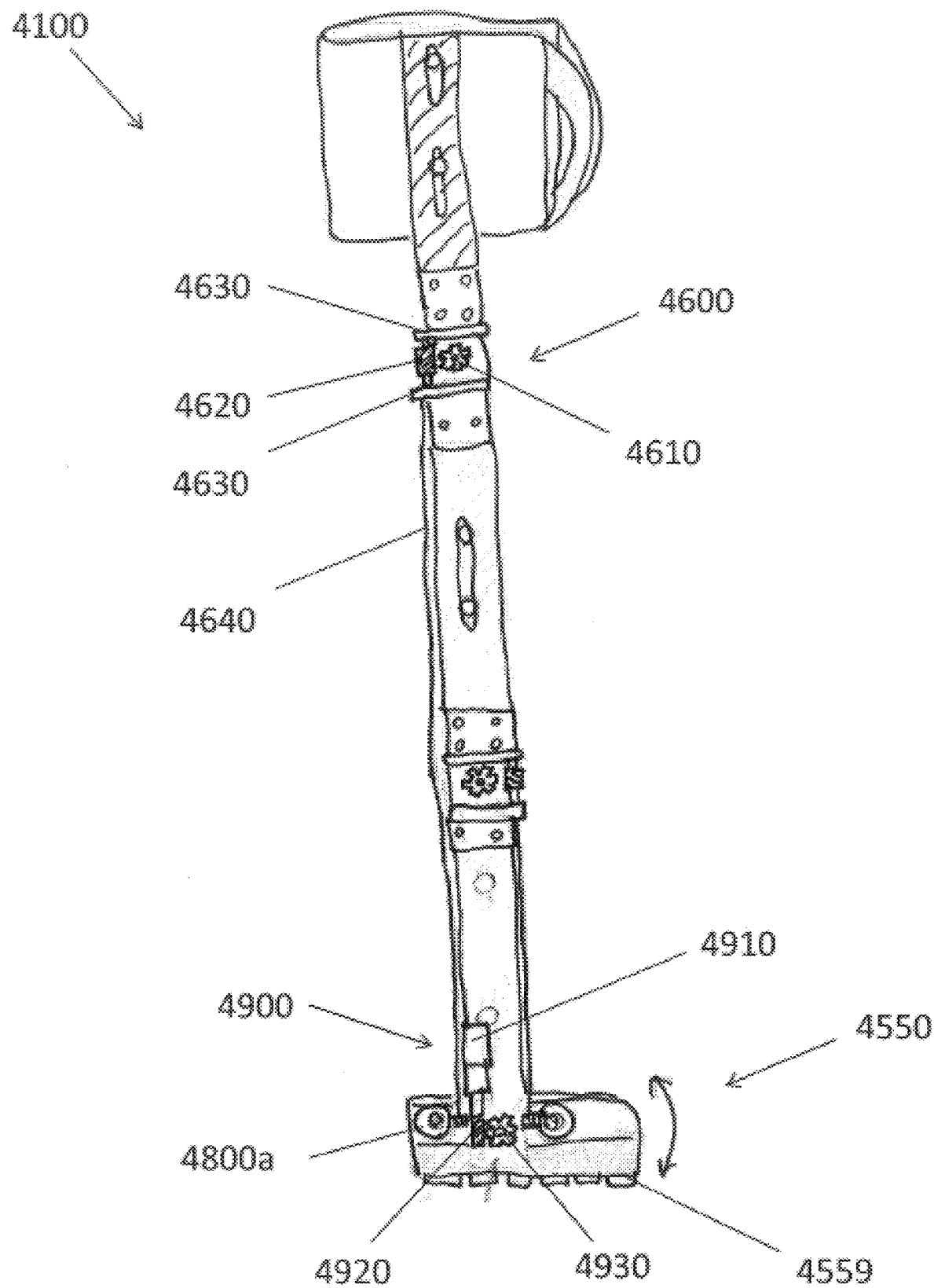
FIG. 16 illustrates an exoskeleton with a drive mechanism according to a further embodiment of the disclosure.

FIG. 16 illustrates another embodiment of an exoskeleton 4100. Exoskeleton 4100 may be substantially identical to exoskeleton 100 with the exception of the following items. Instead of spindle joints, exoskeleton 4100 may include worm drive joints. For example, hip actuator 4600 may include a worm gear 4610 which is coupled to the upper and lower leg panels and the rotation of which actually causes rotation of the panels. Hip actuator 4600 may also include a worm screw 4620 coupled to bearing blocks 4630. Bearing blocks 4630 may function to keep worm screw 4620 in a fixed angular relation to worm gear 4610. A cable 4640 rigid enough to transmit torque, such as a flex shaft, may be operatively coupled to worm screw 4620, such that rotation of cable 4640 causes rotation of worm screw 4620. Cable 4640 may be routed to foot module 4550, to an actuator 4800a. Actuator 4800a may include a motor that rotates a shaft that causes, in turn, cable 4640 to rotate. The torque on cable 4640 is transmitted to worm screw 4620, which meshes with worm gear 4610. Ultimately, the power supplied by the motor of actuator 4800a causes worm gear 4610 to rotate, thus causing hip actuator 4600 to flex or extend. Although the elements are not labeled separately in FIG. 16, the knee actuator may work on the same principles with a separate worm drive, cable, actuator and motor.

Still referring to FIG. 16, an additional actuator 4900 may be supplied on the lower leg panel. Actuator 4900 may include a vertical motor 4910 that directly drives a worm screw 4920 that meshes with a worm gear 4930. Worm gear 4930 may rotatable couple the lower leg panel to foot module 4550, such that rotation of foot module 4550 at the ankle joint can be controlled with by the motor 4910. Additionally, foot module 4559 may include a plurality of ground contacting components 4559, which may be rubber compartments. For example, foot module 4550 may include an array of ground contacting components 4559 which each include sensors, such as pressure sensors, so that the way in which the user's weight is distributed on foot module 4550 can be determined. As should be understood from the descriptions above, this may aid a processor in determining whether and how to actuate motors to facilitate the user completing a particular motion.

Figure 17:
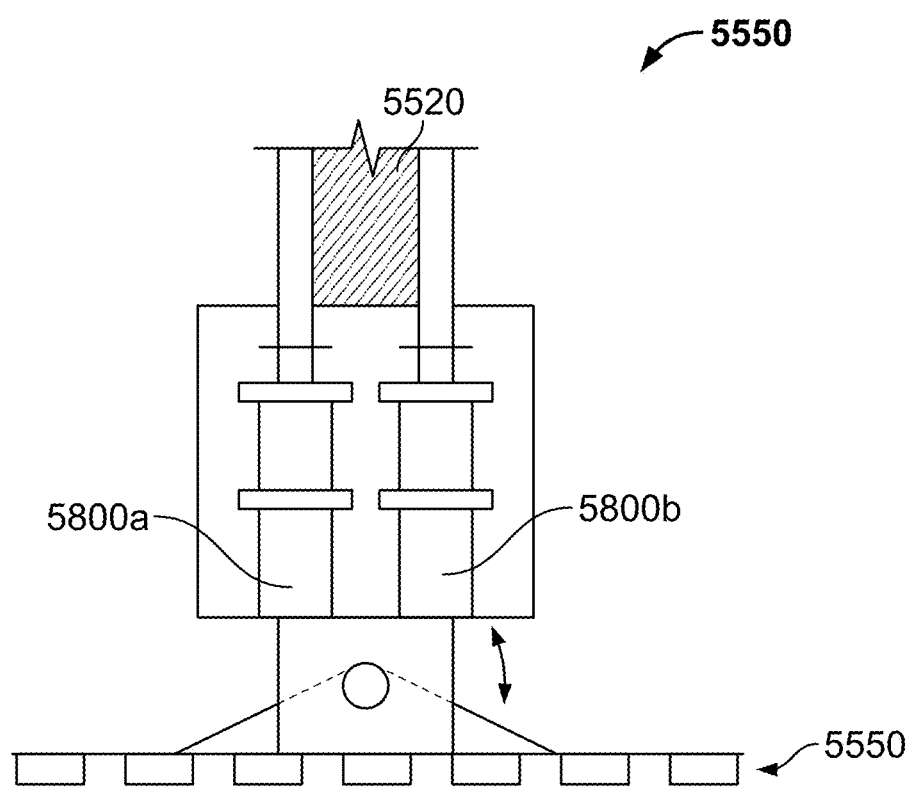
FIG. 17 illustrates a compartment with drive components that may be used for embodiments of an exoskeleton.

FIG. 17 illustrates the lower portion of an embodiment of an exoskeleton with drive mechanism using a cable capable of transmitting torque, similar to that described in connection with FIG. 16. However, with exoskeleton 4100 of FIG. 16, the driving components are positioned within a foot module 4550. The exoskeleton of FIG. 17 includes a low profile foot module 5550. Foot module 5550 may include ground-contact members with sensors similar to that described in connection with exoskeleton 4100, but foot module 5550 is low profile and does not include a compartment to house motors. Rather, similar to the embodiment shown in FIG. 11, the drive mechanism is housed within a compartment coupled to the lower leg panel 5520. Inside the compartment is a first motor 5800a and a second motor 5800b. Each motor 5800a and 5800b is directly coupled to a cable that is capable of transmitting torque. The actuation of motors 5800a and 5800b, and their associated cables, would drive corresponding hip and knee joints in a similar manner to that described in connection with FIG. 16. As should be clear from FIG. 17, foot module 5550 may include a mechanism for rotation at the ankle joint, such as one similar to the embodiment described in connection with FIG. 14A-B.

Figure 18:
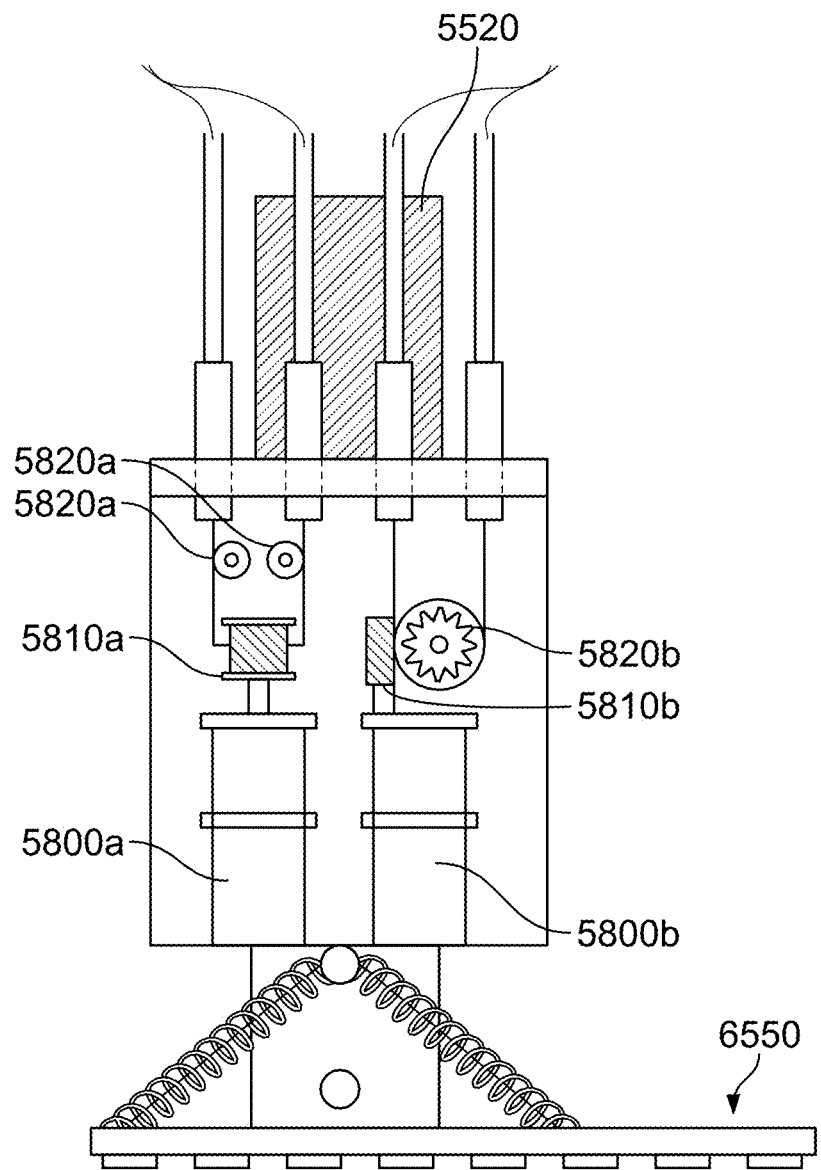
FIG. 18 illustrates a compartment with different drive components that may be used for embodiments of an exoskeleton.

FIG. 18 illustrates the lower portion of yet a further embodiment of an exoskeleton with a joint actuation mechanism similar to the spindle systems described in connection with exoskeleton 100. A foot module 6550 may take a similar form as shown in FIG. 17, with a rotatable ankle joint and the foot module 6550 being low profile without a compartment to house the motors to drive the exoskeleton. A compartment housing the motors to drive the exoskeleton may be coupled to the lower leg panel 5520. Two actuator systems, one including motor 5800a and one including motor 5800b are illustrated. It should be understood that, although different types of actuator systems are shown, in practice a compartment may contain two actuator systems similar to the one including motor 5800a, two actuator systems similar to one including motor 5800b, or one of each as illustrated.

The actuator system including motor 5800b directly drives a worm screw 5810b, which meshes with, and in turn rotates, a worm gear 5820b. Worm gear 5820b may be coupled to a spindle similar to spindle 810b of exoskeleton 100, around which a single wire is wrapped, although multiple wires may be used as described in connection with other embodiments above. The ends of the wires are fed to a spindle of a joint substantially identically to that described in connection with exoskeleton 100. Rotation of the worm screw 5810b in a first direction will cause flexion of the corresponding joint, while rotation of the worm screw 5810b in the opposite direction will cause extension of the corresponding joint.

The actuator system including motor 5800a directly drives spindle 5810a, around which a wire is wrapped. The ends of the wires are each fed to a spindle of a joint substantially identically to that described in connection with exoskeleton 100. Because of the orientation of spindle 5810a, this actuation system preferably includes guide members so that the wire exits the spindle substantially horizontally, and is then fed substantially vertically through the terminator couplings on the top of the compartment. The guide members may be pulleys 5820a. Preferably, one pulley 5820a corresponds to one terminator coupling, and the other pulley 5820a corresponds to the other terminator coupling. Although not drawn to scale, it is preferably that the wire is routed off of spindle 5810a substantially horizontally to pulley 5820a. The wire wraps around pulley 5820a and is then guided vertically through the terminator coupling and to a spindle of a joint. The other pulley 5820a is substantially identical, but positioned on the opposite side of spindle 5810a and routes the wire to the other spindle of the same joint. With this configuration, actuation of motor 5800a may rotate spindle 5810a in a first direction to cause flexion of the associated joint or in the opposite direction to cause extension of that joint. This compartment may be useful, for example, in driving exoskeletons 100' or 100" of FIGS. 11 and 12, respectively.

Finally, although certain components of exoskeleton 100, or variations thereof, are described with reference to a first leg support structure, unless explicitly noted otherwise herein, a substantially identical component, whether or not in a mirrored configuration, may be included in the exoskeleton system on a second leg support structure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, elements of one described embodiment may be combined with elements of another described embodiment without departing from the scope of the invention.

The invention claimed is:

1. A mobility assistive device comprising:
    a torso support and two leg supports coupled to the torso support; each leg support comprising:
        a hip joint;
        a knee joint;
        a foot support;
        a first structure coupling the torso support to the hip joint;
        a second structure coupling the hip joint to the knee joint;
        a third structure coupling the knee joint to the foot support; and
        a compartment having a discrete hip joint actuation device and a discrete knee joint actuation device,
    wherein the hip joint actuation device is operably coupled to the hip joint, the hip joint actuation device configured to drive both flexion and extension of the hip joint; and
    wherein the knee joint actuation device is operably coupled to the knee joint, the knee joint actuation device configured to drive both flexion and extension of the knee joint,
    wherein the foot support includes an upper platform coupled to a lower platform, the compartment positioned within an interior volume between the upper and lower platforms of the foot support,
    wherein each of the hip and knee joint actuation devices comprises an actuation spindle and an actuator,
    wherein the hip joint includes a hip extension spindle coupled to a hip flexion spindle, each of the hip extension spindle and hip flexion spindle operatively coupled to the hip joint actuation device via a single hip cable,
    wherein the knee joint includes a knee extension spindle coupled to a knee flexion spindle, each of the knee extension spindle and knee flexion spindle operatively coupled to the knee joint actuation device via a single knee cable,
    wherein the mobility enhancing device is in the form of a low profile exoskeleton.

2. The device of claim 1, wherein the single hip cable is configured to transmit power from the hip joint actuation device for driving both flexion and extension of the hip joint.

3. The device of claim 1, wherein at least a portion of the single hip cable is housed within a tube-like hollow conduit, the single hip cable configured to move through the tube-like hollow conduit.

4. The device of claim 1, wherein the single knee cable is configured to transmit power from the knee joint actuation device for driving both flexion and extension of the knee joint.

5. The device of claim 1, wherein at least a portion of the single knee cable is housed within a tube-like hollow conduit, the single knee cable configured to move through the tube-like hollow conduit.

6. The device of claim 1, wherein the hip extension spindle is configured to rotate in a first direction to cause extension of the first structure relative to the second structure, the hip flexion spindle is configured to rotate in a second direction opposite the first direction to cause flexion of the first structure relative to the second structure.

7. The device of claim 6, wherein a first end of the single hip cable is coupled to the hip flexion spindle and a second end of the single hip cable is coupled to the hip extension spindle, a middle portion of the single hip cable being operably coupled to the hip joint actuation device, the single hip cable configured to transmit power from the hip joint actuation device for driving both flexion and extension of the hip joint.

8. The device of claim 1, wherein the knee extension spindle is configured to rotate in a first direction to cause extension of the second structure relative to the third structure, the knee flexion spindle is configured to rotate in a second direction opposite the first direction to cause flexion of the second structure relative to the third structure.

9. The device of claim 8, wherein a first end of the single knee cable is coupled to the knee flexion spindle and a second end of the single knee cable is coupled to the knee extension spindle, a middle portion of the single knee cable being operably coupled to the knee joint actuation device, the single knee cable configured to transmit power from the knee joint actuation device for driving both flexion and extension of the knee joint.

10. The device of claim 1, wherein the second structure coupling the hip joint to the knee joint includes a first panel configured to be adjustably coupled to a second panel, the first panel being coupled to the hip joint and the second panel being coupled to the knee joint.

11. The device of claim 1, wherein the third structure coupling the knee joint to the foot support includes a first panel configured to be adjustably coupled to a second panel, the first panel being coupled to the knee joint and the second panel being coupled to the foot support.

12. The device of claim 1, wherein the first structure includes an inferior first support bracket and the second structure includes a superior second support bracket, the inferior first support bracket and superior second support bracket having a first set of corresponding surfaces for limiting a maximum extension of the hip joint and a second set of corresponding surfaces for limiting a maximum flexion of the hip joint.

13. The device of claim 1, wherein the second structure includes an inferior second support bracket and the third structure includes a superior third support bracket, the inferior second support bracket and superior third support bracket having a first set of corresponding surfaces for limiting a maximum extension of the knee joint and a second set of corresponding surfaces for limiting a maximum flexion of the knee joint.

14. The device of claim 1, wherein the foot support includes at least one sensor selected from the group consisting of weight sensors, inertial measurement unit sensors, and accelerometers.

* * * * *